(12) United States Patent
Yanev et al.

(10) Patent No.: US 11,097,155 B2
(45) Date of Patent: Aug. 24, 2021

(54) EXERCISE SYSTEMS, METHODS, AND APPARATUSES CONFIGURED FOR EVALUATING MUSCULAR ACTIVITY OF USERS DURING PHYSICAL EXERCISE AND/OR PROVIDING FEEDBACK TO USERS

(71) Applicant: Activbody, Inc., Aliso Viejo, CA (US)

(72) Inventors: Kostadin Dimitrov Yanev, Monte-Carlo (MC); Ivo Kostadinov Yanev, Sofia (BG); Angel Georgiev Vassilev, Aliso Viejo, CA (US)

(73) Assignee: ACTIVBODY, INC., San Diego, CA (US)

( * ) Notice: Subject to any disclaimer, the term of this patent is extended or adjusted under 35 U.S.C. 154(b) by 184 days.

(21) Appl. No.: 15/521,167

(22) PCT Filed: Dec. 30, 2015

(86) PCT No.: PCT/US2015/068143
§ 371 (c)(1),
(2) Date: Apr. 21, 2017

(87) PCT Pub. No.: WO2016/109719
PCT Pub. Date: Jul. 7, 2016

(65) Prior Publication Data
US 2018/0064991 A1 Mar. 8, 2018

Related U.S. Application Data

(63) Continuation-in-part of application No. 14/588,257, filed on Dec. 31, 2014, now abandoned.

(51) Int. Cl.
| | |
|---|---|
| A63B 24/00 | (2006.01) |
| A63B 21/00 | (2006.01) |
| A63B 21/04 | (2006.01) |
| G16H 20/30 | (2018.01) |
| A63B 71/06 | (2006.01) |

(Continued)

(52) U.S. Cl.
CPC .... *A63B 24/0006* (2013.01); *A63B 21/00181* (2013.01); *A63B 21/023* (2013.01);
(Continued)

(58) Field of Classification Search
CPC . A63B 24/0006; A63B 23/0405; A63B 23/12; A63B 23/129; A63B 21/4011;
(Continued)

(56) References Cited

U.S. PATENT DOCUMENTS

| | | |
|---|---|---|
| 5,139,261 A | 8/1992 | Openiano |
| 5,341,680 A | 8/1994 | Smart et al. |

(Continued)

OTHER PUBLICATIONS

European Patent Office, Supplementary European Search Report for EP 15876294.8, dated Jul. 13, 2018, pp. 1-9.

(Continued)

*Primary Examiner* — Sundhara M Ganesan
*Assistant Examiner* — Shila Jalalzadeh Abyaneh
(74) *Attorney, Agent, or Firm* — Pillsbury Winthrop Shaw Pittman LLP

(57) ABSTRACT

The present disclosure describes systems, methods, and apparatus that facilitate exercise. The system may include one or more convenient, fun, easy to use and low impact exercise apparatuses. An exercise apparatus may comprise one or more physical user interface components configured to engage one or more body parts of the user. The user may perform exercises by exerting forces on individual ones of the one or more user interface components. In some implementations, gameplay may be incorporated into one or more exercises through a game interface presented to the users. Users may be coached during gameplay to perform one or more exercises such that exercise and gameplay may be seamlessly integrated.

17 Claims, 9 Drawing Sheets

(51) Int. Cl.
*A63B 21/16* (2006.01)
*A63B 23/04* (2006.01)
*A63B 21/055* (2006.01)
*A63B 23/12* (2006.01)
*A63B 21/02* (2006.01)

(52) U.S. Cl.
CPC ...... *A63B 21/0442* (2013.01); *A63B 21/0552* (2013.01); *A63B 21/154* (2013.01); *A63B 21/1609* (2015.10); *A63B 21/4001* (2015.10); *A63B 21/4011* (2015.10); *A63B 21/4013* (2015.10); *A63B 23/04* (2013.01); *A63B 23/0405* (2013.01); *A63B 23/12* (2013.01); *A63B 23/129* (2013.01); *A63B 24/0062* (2013.01); *G16H 20/30* (2018.01); *A63B 2024/0065* (2013.01); *A63B 2024/0068* (2013.01); *A63B 2024/0071* (2013.01); *A63B 2071/065* (2013.01); *A63B 2071/0655* (2013.01); *A63B 2220/16* (2013.01); *A63B 2220/52* (2013.01); *A63B 2220/54* (2013.01); *A63B 2220/56* (2013.01); *A63B 2220/803* (2013.01); *A63B 2220/836* (2013.01); *A63B 2230/62* (2013.01); *A63B 2230/75* (2013.01)

(58) Field of Classification Search
CPC ... A63B 21/4013; A63B 21/023; A63B 23/04; A63B 21/1609; A63B 21/154; A63B 21/0552; A63B 21/4001; A63B 21/0442; A63B 24/0062; A63B 21/00181; A63B 2230/62; A63B 2220/54; A63B 2071/065; A63B 2024/0071; A63B 2071/0655; A63B 2220/16; A63B 2024/0068; A63B 2024/0065; A63B 2230/75; A63B 2220/52; A63B 2220/56; A63B 2220/803; A63B 2220/836; G16H 20/30
See application file for complete search history.

(56) References Cited

U.S. PATENT DOCUMENTS

| | | | |
|---|---|---|---|
| 5,398,696 A | 3/1995 | Wiley | |
| 6,086,518 A | 7/2000 | MacCready | |
| 6,436,058 B1* | 8/2002 | Krahner | G16H 20/30 600/587 |
| 10,398,938 B2* | 9/2019 | Vardy | A61B 5/1036 |
| 2002/0143277 A1 | 10/2002 | Wood et al. | |
| 2003/0093012 A1 | 5/2003 | Smyser et al. | |
| 2004/0039254 A1 | 2/2004 | Stivoric et al. | |
| 2004/0176226 A1 | 9/2004 | Carlson | |
| 2007/0066451 A1 | 3/2007 | Gruben et al. | |
| 2007/0232450 A1 | 10/2007 | Hanoun | |
| 2008/0119337 A1 | 5/2008 | Wilkins et al. | |
| 2008/0132388 A1 | 6/2008 | Clem et al. | |
| 2008/0287816 A1 | 11/2008 | Honda | |
| 2009/0047645 A1 | 2/2009 | Dibenedetto et al. | |
| 2009/0098980 A1 | 4/2009 | Waters | |
| 2010/0004061 A1* | 1/2010 | Merril | A63B 21/023 463/36 |
| 2011/0241860 A1 | 10/2011 | Andrews | |
| 2011/0269601 A1* | 11/2011 | Nelson | A47C 31/126 482/8 |
| 2012/0116258 A1* | 5/2012 | Lee | A61B 5/1071 600/595 |
| 2013/0337976 A1* | 12/2013 | Yanev | A61B 5/103 482/8 |
| 2014/0200470 A1 | 7/2014 | Puolakanaho et al. | |
| 2014/0240132 A1 | 8/2014 | Bychkov | |
| 2015/0301613 A1* | 10/2015 | Yanev | A61B 5/6897 463/31 |
| 2015/0321067 A1* | 11/2015 | Wright | A63B 71/00 434/247 |
| 2016/0361597 A1* | 12/2016 | Cole | A63F 13/245 |
| 2017/0232297 A1 | 8/2017 | Prokhorov | |
| 2018/0190248 A1 | 7/2018 | Paranjpe et al. | |

OTHER PUBLICATIONS

U.S. Patent and Trademark Office, Non-Final Office Action in related U.S. Appl. No. 15/657,913, dated Jun. 13, 2019, pp. 1-15.
European Patent Office, European Office Action for EP Application No. 15876294.8, dated Mar. 11, 2020, pp. 1-3.
United States Patent and Trademark Office, U.S. Office Action for U.S. Appl. No. 15/657,913, dated Feb. 20, 2020.

* cited by examiner

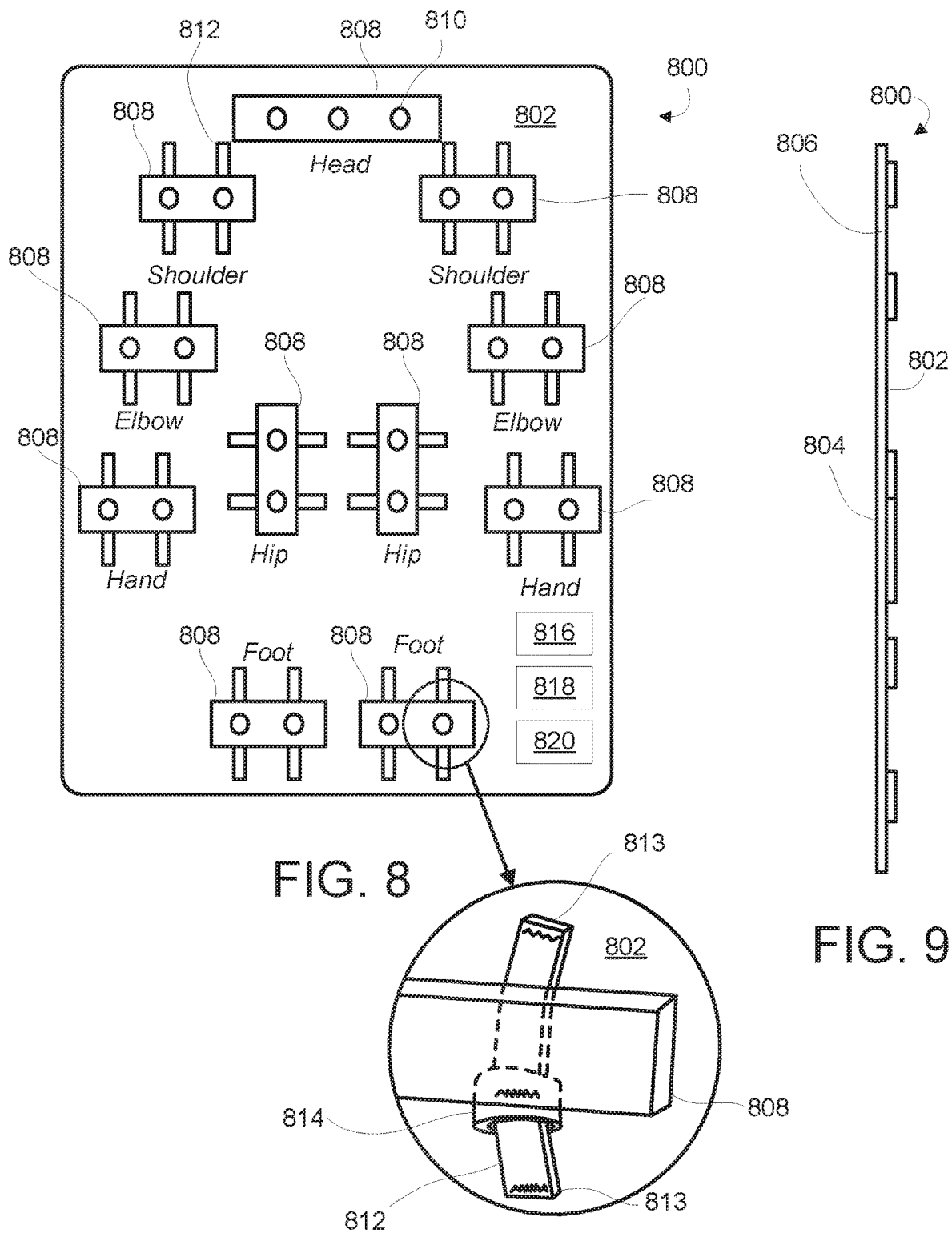

EXERCISE SYSTEMS, METHODS, AND APPARATUSES CONFIGURED FOR EVALUATING MUSCULAR ACTIVITY OF USERS DURING PHYSICAL EXERCISE AND/OR PROVIDING FEEDBACK TO USERS

CROSS REFERENCE TO RELATED APPLICATIONS

The present application is the National Phase of International Application No. PCT/US2015/068143, filed Dec. 30, 2015, which is a Continuation-in-Part of and claims priority to U.S. application Ser. No. 14/588,257, filed Dec. 31, 2014, entitled "EXERCISE SYSTEMS, METHODS, AND APPARATUSES CONFIGURED FOR EVALUATING MUSCULAR ACTIVITY OF USERS DURING PHYSICAL EXERCISE AND/OR PROVIDING FEEDBACK TO USERS", the entire content of which is incorporated herein by reference.

FIELD OF THE DISCLOSURE

The present disclosure relates to exercise systems, methods, and apparatuses configured for evaluating muscular activity of users performing one or more physical exercises and/or for providing feedback to users during performance of one or more physical exercises.

BACKGROUND

Individuals tend to participate in physical exercise when it is convenient. If a user can seamlessly integrate exercise into their daily routine, they may exercise more frequently and enjoy the health benefits that follow.

SUMMARY

One or more aspects of the disclosure relates to a system that facilitates exercise through the use of one or more convenient, fun, easy to use, and low impact exercise apparatuses. In some implementations, gameplay may be incorporated into one or more exercises through a game interface presented to the users. Gameplay may include controlling game entities within a game. Users may exert forces on one or more physical components of an exercise apparatus to provide control inputs for a corresponding game entity. Users may be coached during gameplay to perform one or more exercises such that exercise and gameplay may be seamlessly integrated.

One or more aspects of the disclosure relate to a system for evaluating muscular activity of a user during exercise and/or providing feedback to the user. The system may include an exercise apparatus configured to engage a user in a substantially seated position and/or other position. For example, the exercise apparatus may include a portion that resembles a chair. The exercise apparatus may comprise one or more physical user interface components configured to engage one or more body parts of the user while in the substantially seated position and/or other position. The user may perform exercises by exerting forces on individual ones of the one or more user interface components. In some implementations, the exercise apparatus may include one or more repositionable sensor configurations. A user may perform exercise using the apparatus by exerting forces on individual ones of the repositionable sensor configurations.

The system may include one or more sensors configured to generate output signals. The output signal may convey information related to one or more parameters of muscular activity of the user during the exercises and/or other information. The parameters may correspond to one or more of a muscle and/or muscle group activated by the user during performance of a given exercise, an amount of force exerted by the muscle and/or muscle group during a given exercise, an amount of repetitions of activation of the muscle and/or muscle group, an elapsed time of performance of a given exercise, an amount of energy expended (e.g., calories burned), and/or other parameter of muscular activity. Individual ones of the one or more sensors may be coupled to corresponding individual ones of the one or more user interface components and/or sensor configurations.

In some implementations, output signals of a sensor may convey information that may be used to determine and/or express a quantification of exertion by a user. The quantification of exertion may include a quantification of one or more measures. Examples of such measures may include one or more of force, pressure, energy, power, duration, displacement, acceleration, and/or other measure useful in quantifying exertion. Force may be expressed in units of Newtons, pounds (force), Dyne, Ton-force, kilogram-force, Kip, and/or other units of force. Pressure may be expressed in units of Pascals, pounds per square inch (PSI), Bar, Torr, atmosphere, and/or other units of pressure. Energy may be expressed in units of calories, joules, horsepower-hour, foot-pound force, body fat equivalent, and/or other units of energy. Body fat equivalent ("BFE") may be an energy measure that shows the user how much energy was expended in terms of body fat (e.g., how much body fat was burned during a given exercise or exercise session). Power may be expressed in units of watts, horsepower, and/or other units of power. The quantification of exertion may provide continuous and/or discrete values of measures related to the application of force by a user during exercise. The values of measures may be expressed as a function of time. By way of non-limiting example, a sensor may generate output signals conveying an amount of force exerted by the user at or near the sensor. To illustrate, a user may press their hand at or near a sensor and that sensor may generate output signals conveying information related to an amount of force exerted by the user's hand. By way of non-limiting example, a sensor may generate output signals conveying discrete predetermined force levels based on an amount of force exerted by the user meeting or exceeding the predetermined force levels. To illustrate, a user may press their hand at or near a sensor using a first level of force for some duration and using a second level of force for a later duration, the first level of force being less than the second level of force.

The one or more sensors may be configured to communicatively couple with one or more physical processors. The one or more processors may be disposed at an exercise apparatus, a computing platform, a remote server, and/or other locations in the system.

The system may include one or more feedback components. A feedback component may include one or more components configured to provide one or more of visual feedback, auditory feedback, tactile feedback, olfactory feedback, and/or other feedback. A feedback component may be disposed at an exercise apparatus, a computing platform, and/or other location.

The one or more processors may be configured to execute one or more computer program components. The computer program components may include computer-readable instructions stored on storage media. The computer program components may include one or more of a communication component, a space component, a user component, a coach component, an interface component, and/or other computer program components.

The communication component may be configured to facilitate information communication between computer program components of the processor(s), between one or more computer program components and an entity external to the processor(s) (e.g., a feedback component, a sensor, and/or other entity), and/or may facilitate other information exchanges. In some implementations, the communication component may be configured to obtain output signals associated with the one or more sensors.

The space component may be configured to execute an instance of a game and implement the instance of the game to facilitate user participation in the game that takes place in a virtual space. User participation in the game may include controlling game entities within the virtual space.

The user component may be configured to access and/or manage user profiles associated with the users of the system. The user component may be configured to determine values for the one or more parameters of muscular activity for the users based on the output signals (e.g., obtained by the communication component). The user component may be configured to provide the determined values as control inputs for controlling the game entities in the virtual space (e.g., via the space component).

The coach component may be configured to effectuate presentation of exercise instruction to a user via one or more feedback components. The instruction may be related to coaching a user to perform one or more exercises. For example, the instruction may be related to coaching a user on exerting forces on the exercise apparatus using one or more muscles and/or muscle groups. The coach component may be configured to modify the presented exercise instruction based on the values of the parameters of muscular activity determined by the user component. The modification may include changing the instruction based on a user successfully following instruction, repeating instruction and/or changing one or more aspects of the instruction to encourage a user to successfully perform an exercise, and/or other modification. For example, the modification may correspond to coaching a user to continue exerting forces using a given muscle and/or muscle group or to exert forces using a different muscle and/or muscle group.

The interface component may be configured to effectuate presentation of an interface via a feedback component (e.g., a display and/or screen). The interface may include views of a virtual space and/or game executed by the space component and/or other information.

One or more aspects of the disclosure relate to systems and methods for coaching a user to perform one or more exercises. Coaching a user may comprise operations including: effectuating presentation of exercise instruction via one or more feedback components; obtaining output signals from one or more sensors coupled to an exercise apparatus; determining values for the one or more parameters of muscular activity based on the output signals; modifying the presented exercise instruction based on the determined values; and/or other operations.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular forms of "a", "an", and "the" include plural referents unless the context clearly dictates otherwise.

BRIEF DESCRIPTION OF THE DRAWINGS

FIG. 8 illustrates another exemplary implementation of an exercise apparatus.

FIG. 8a illustrates a detailed view of an exemplary repositionable sensor configuration used in the exercise apparatus of FIG. 8.

FIG. 9 illustrates a side view of the implementation of the exercise apparatus of FIG. 8.

DETAILED DESCRIPTION

Figure 1:
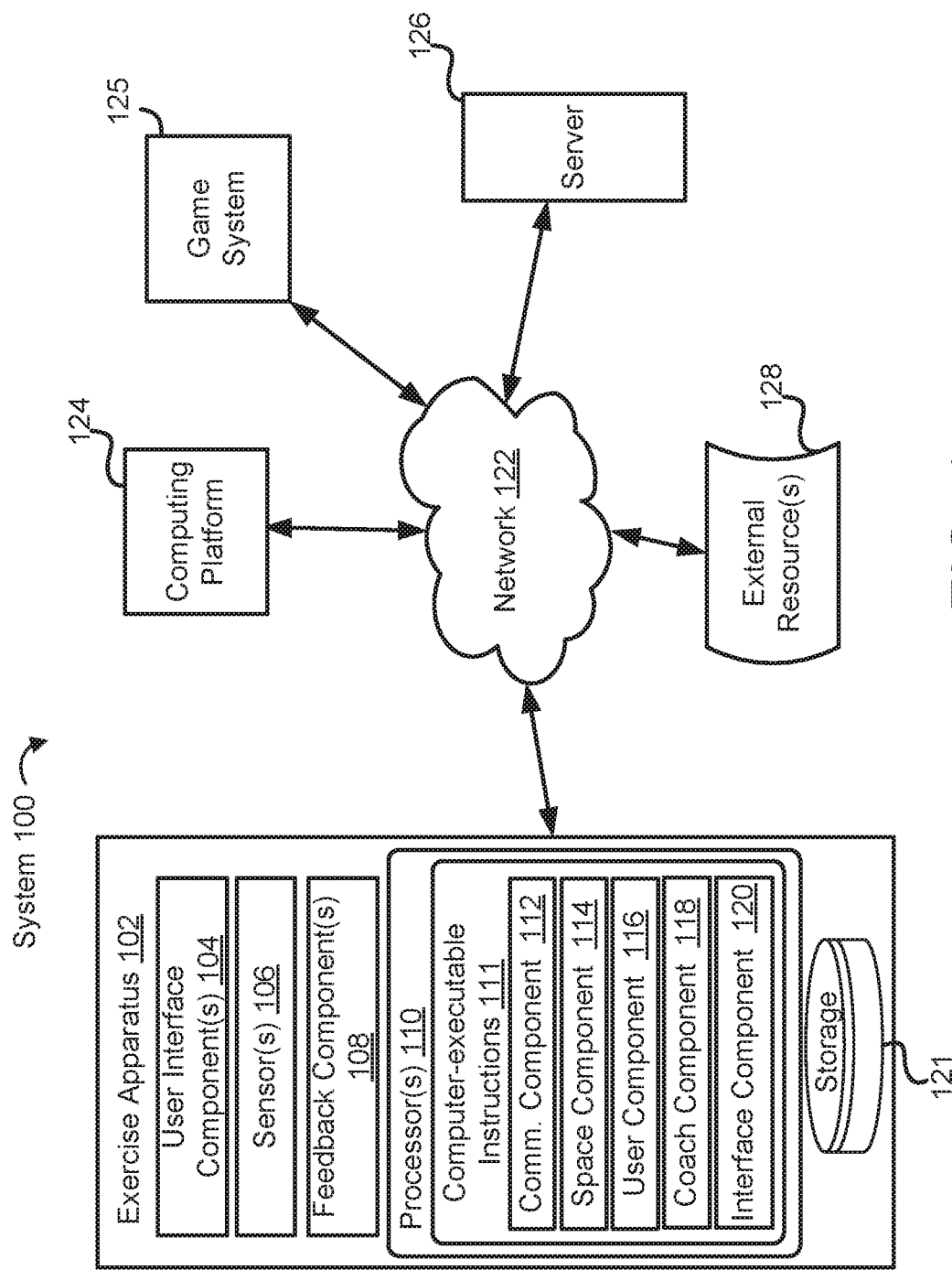
FIG. 1 illustrates a system configured for evaluating muscular activity of a user during exercise and/or providing feedback to the user, in accordance with one or more implementations.

FIG. 1 illustrates an exercise system 100 configured for evaluating muscular activity of a user and/or providing feedback to the user, in accordance with one or more implementations. In some implementations, the system 100 may facilitate exercise via a game to encourage users to perform exercise(s).

In some implementations, system 100 may include an exercise apparatus 102, one or more processors 110 configured to execute computer-executable instructions 111, and/or other components. In some implementations, the one or more processors 110 may be disposed at the exercise apparatus 102 (see, e.g., FIG. 1 and FIG. 2). In some implementations, the one or more processors 110 may be disposed at a computing platform 124 (see, e.g., FIG. 3), remote server 126, and/or other locations in system 100. The computing platform(s) 124 may include, for example, a cellular telephone, a smartphone, a laptop, a tablet computer, a desktop computer, a television set-top box, a smart TV, a gaming console, and/or other computing platform.

In some implementations, the exercise apparatus 102 may facilitate performance of physical exercises including isometric exercise, dynamic exercise, aerobic exercise, anaerobic exercise, flexibility exercise, stretching, resistance exercise, and/or other physical exercise. A given exercise may include performing certain body motions and/or assuming certain body poses. The exercise apparatus 102 may comprise one or more user interface components 104, one or more sensors 106, and/or other components. The user interface component(s) 104 may include physical components. The user interface component(s) 104 may be removable from the exercise apparatus 102. The user interface component(s) 104 may be moveable and/or repositionable upon the exercise apparatus 102. The user interface component(s) 104 may be immovably disposed upon the exercise apparatus 102. The user interface component(s) 104 may be configured to receive forces exerted by a user during performance of one or more exercises.

The user interface component(s) 104 may be configured and/or arranged to engage one or more body parts of the user and/or be positioned/repositioned in an arrangement compatible with a user imparting forces thereon during exercise. In some implementations, the one or more user interface component(s) 104 may include components configured and/or arranged to engage one or more of a finger, a hand, a wrist, an elbow, an arm, a torso, a head, a shoulder, a hip, a thigh, a knee, a calf, an ankle, a foot, and/or any other body part of the user. By way of non-limiting example, a user may impart a force onto one or more user interface components 104 by pressing, pulling, pushing, squeezing, lifting, striking, shaking, twisting, turning, separating, and/or otherwise imparting a force onto one or more of the user interface components 104 or portions thereof. By way of additional non-limiting example, a user may impart a force onto a user interface component 104 configured to engage a hand of a user by squeezing the user interface component 104 (e.g., the user interface component 104 may be hand grip).

In some implementations, individual ones of one or more sensors 106 may be coupled to corresponding ones of the one or more user interface components 104. For example, a first sensor may be coupled to a first user interface component. By way of non-limiting example, one or more sensors 106 may be coupled to a user interface component 104 configured and/or arranged to engage a hand of a user; one or more sensors 106 may be coupled to a user interface component 104 configured and/or arranged to engage an arm of a user; one or more sensors 106 may be coupled to a user interface component 104 configured to engaged a knee or thigh of a user; and/or other sensors 106 may be coupled to other user interface components 104. It is noted that the above example of various arrangements of sensors 106 and/or user interface components 104 is not to be considered limiting. Instead, it is merely provided as an illustrative example and should not limit the manner in which one or more sensors 106 may be coupled to one or more user interface components 104.

In some implementations, the sensor(s) 106 may be configured to generate output signals conveying information related to one or more parameters of muscular activity of the user performing one or more exercises, and/or other information. Parameters of muscular activity may include one or more of an exercise parameter corresponding to a given exercise performed by the user; a muscle activation parameter corresponding to a muscle and/or muscle group activated by a user during performance of a given exercise; a force parameter corresponding to an amount of force exerted by a muscle and/or muscle group during a given exercise; a repetition parameter corresponding to an amount of repetitions of activation of a muscle and/or muscle group by a user during a given exercise; a time parameter corresponding to an elapsed time of performance of a given exercise and/or an elapsed time between repetitions; an energy parameter corresponding to an amount (e.g., average, total, current, and/or other amount) of energy expenditure by the user during a given exercise and/or repetition ("rep"), and/or other parameter (see, e.g., user component 116 described herein).

The one or more sensors 106 may be configured to communicatively couple (e.g., wired or wirelessly) with the one or more physical processors 110. In implementations where the one or more processors 110 may be disposed at a computing platform 124 (see, e.g., FIG. 3), the one or more sensors 106 may be configured to communicate with the one or more processors 110 over network 122, and/or over other communication networks. In implementations where the one or more processors 110 may be disposed at the exercise apparatus 102 (see, e.g., FIG. 1 and FIG. 2), the one or more sensors 106 may be configured to communicate with the one or more processors 110 via communications routed locally within the exercise apparatus 102, and/or over other communication networks. The one or more physical processors 110 may be configured to obtain the sensor output signals, determine values for the one or more parameters, and/or perform other functions described herein.

The one or more sensors 106 may be configured for wired and/or wireless communication. By way of non-limiting example, the one or more sensors 106 may be configured for wired communication via a port or a drive disposed at a given sensor 106. A port disposed at the sensor(s) 106 may include a USB port, a firewire port, and/or other port. By way of non-limiting example, the one or more sensors 106 may be configured for wireless communication via Bluetooth, near-field communication, infrared, Wi-Fi, and/or other wireless communication protocol.

In some implementations, a given sensor may comprise a sensor configured to measure one or more of force, torque, strain, displacement, position, compression, temperature, pressure, contact, and/or other measurement. For example, a sensor may comprise one or more of a strain measurement sensor, a force-sensing resistor, a force-sensitive material, a load sensor, a pressure sensor, a load cell, a touch sensor, a position sensor, a temperature sensor, and/or other sensor.

In some implementations, the sensor(s) 106 may comprise one or more sensors that generate output signals used to determine values for the parameters directly or indirectly. For example, a first sensor may generate a first output signal(s) used to determine, directly or indirectly, a first value of a first parameter. In some implementations, a sensor may be configured to generate output signals directly related to force applied at or near the sensor, and/or other output. By way of non-limiting example, a given force-measuring sensor may be disposed at a location on a corresponding user interface component 104 configured to be pushed by a hand of a user. The force measurement sensor may generate output signals directly related to a force applied to the user interface component 104. The output signals may directly provide a value of a force parameter associated with the user, and/or other parameter. By way of non-limiting example, a touch sensor may generate sensor output related to instances of contact with the sensor and/or user interface component 104 at or near the sensor. Sensor output from the touch sensor may include a count of an amount of times the sensor is "touched" or otherwise activated. The sensor output may directly provide a value of a repetition parameter associated with repetitive activation of a muscle and/or muscle group. In some implementations, other sensors may be configured to generate other output signals that are directly related to values of other parameters corresponding to muscular activity.

In some implementations, a sensor 106 may be configured to generate output signals that may be indirectly related to a value of a parameter. By way of non-limiting example, a position sensor may be configured to generate output signals related to an amount of displacement or deflection of a corresponding user interface component 104. Output signals from a position sensor (e.g., corresponding to an amount of deflection) may be used to determine (e.g., calculate) an amount of force imparted on the user interface component 104 by the user. The determination may be based on an arrangement, configuration, material properties, and/or other attribute of the user interface component 104. By way of non-limiting example, a user interface component 104 may be approximated as a cantilever beam. A determination may be based on calculating an amount of force required to deflect the approximated cantilever beam a measured deflected distance (e.g., based on the output signal). The sensor output may indirectly provide a value of a force parameter, and/or other parameter. By way of non-limiting example, one or more sensors 106 may be configured to generate output signals related to an amount of compression of a user interface component, torsion on a user interface component, strain on a user interface component, and/or other measurement that may be used to determine a parameter value indirectly.

The above description of determining values for one or more parameters of muscular activity either directly or indirectly are not intended to be limiting. Instead, this is provided for illustrative purposes only and is not intended to be limiting with respect to the sensors, configurations and/or arrangement of the user interface components 104, and/or the manner or techniques in which values may be determined.

In some implementations, one or more feedback components 108 may be disposed at the exercise apparatus (see, e.g., FIG. 1 and FIG. 2), and/or other locations. In some implementations, one or more feedback components 108 may be disposed at a computing platform 124 (see, e.g., FIG. 3), and/or other locations. The one or more feedback components 108 may be configured to communicatively couple with the one or more physical processors 110 and/or with other components. The one or more processors 110 may be configured to effectuate presentation of exercise instruction and/or other feedback to the user via one or more feedback components 108 and/or perform other functions. In implementations where the one or more processors 110 may be disposed at a computing platform 124 (see, e.g., FIG. 3), the one or more feedback components 108 may be configured to communicate with the one or more processors 110 over network 122, and/or other communication networks. In implementations where the one or more processors 110 may be disposed at the exercise apparatus 102 (see, e.g., FIG. 1 and FIG. 2), the one or more feedback components 108 may be configured to communicate with the one or more processors 110 via communications routed locally within the exercise apparatus 102, and/or over other communication networks.

The one or more feedback components 108 may comprise a physical component or set of physical components configured to provide one or more of visual feedback, auditory feedback, tactile feedback, olfactory feedback, and/or other feedback to a user. In some implementations, a feedback component 108 may comprise one or more of a display screen, a light source, an audio speaker, a haptic device, a scent apparatus, a heating element, a fan and/or blower, and/or other components. In some implementations, one or more feedback components 108 may be coupled with one or more user input mechanisms (e.g., a button, a mouse, a joystick, a keyboard, and/or other input mechanism).

A feedback component 108 may include a display screen configured to provide visual feedback. A display screen may include a touch sensitive screen configured to receive user entry and/or selection of information. A display screen may be configured to effectuate display one or more of images, video, text, holograms, and/or other visual display. In some implementations, a display may facilitate presentation of an interface used for gaming, and/or other application (see, e.g., FIG. 5 and FIG. 6, described in more detail herein). In some implementations, a display may be disposed at a user interface component 104, a computing platform 124, and/or other locations.

A feedback component 108 may include one or more light sources configured to provide visual feedback. A light source may include one or more of a light emitting diode (LED), a light bulb, a Chemo-luminescent light source, a lamp, a laser, and/or other source of visible (or invisible) light. In some implementations, a light source may be disposed at a user interface component 104, a computing platform 124, and/or other locations.

A feedback component 108 may comprise one or more audio speakers configured to provide audio feedback. A speaker may be configured to emit a sound (e.g., a buzz, a beep, an alarm, and/or other sound), a song, a recording, a recorded voice, a computer-generated voice, and/or other audio. In some implementations, a speaker may be disposed at a user interface component 104, a computing platform 124, and/or other locations.

A feedback component 108 may include one or more haptic devices configured to provide tactile feedback. A haptic device may include a vibrator and/or other haptic device. A vibrator may include an eccentric rotating mass, and/or other components. In some implementations, a haptic device may be disposed at a user interface component 104, a computing platform 124, and/or other locations.

A feedback component 108 may include one or more heating elements configured to provide heat-based feedback. A heating element may be configured to heat, cool, and/or other produce other heat-based feedback. In some implementations, a heating element may be disposed at a user interface component 104, a computing platform 124, and/or other locations.

A feedback component 108 may include one or more fans and/or blowers configured to provide other feedback. A fan and/or blower may be configured to blow air and/or other gas, draw in air and/or other gas, and/or other performs other operations. In some implementations, a fan and/or blower may be disposed at a user interface component 104, a computing platform 124, and/or other locations.

A feedback component 108 may include a scent apparatus configured to generate a scent to provide olfactory feedback. A scent apparatus may include, for example, an apparatus including a vessel for storing a perfume or other scented substance and a discharge/emission element coupled to the vessel configured to discharge/emit an amount of the substance when triggered/activated. By way of non-limiting example, a discharge element may include an atomizing pump, a fan, a blower, and/or other components. A scent apparatus may be considered in other ways. In some implementations, a scent apparatus may be disposed at a user interface component 104, a computing platform 124, and/or other locations in system 100.

In some implementations, the one or more feedback components 108 may be configured to provide feedback in the form of instructional feedback (e.g., coaching), and/or may provide other information to a user. The feedback provided by a feedback component 108 may be positive, neutral, and/or negative feedback, described in more detail herein.

Figure 2:
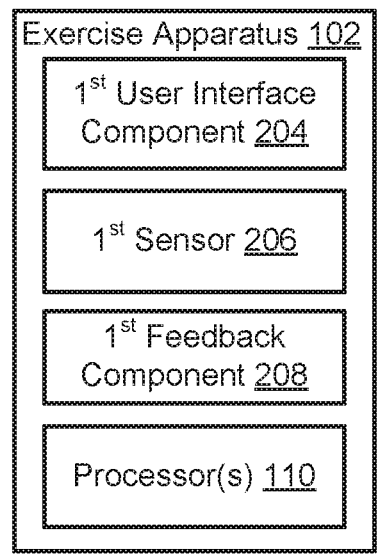
FIG. 2 illustrates an exemplary implementation of an exercise apparatus.

FIG. 2 illustrates an exemplary implementation of an exercise apparatus 102. The exercise apparatus 102 may include a first user interface component 204, a first sensor 206, a first feedback component 208, one or more processors 110, and/or other components. The first sensor 206 may be disposed at the first user interface component 204. The first sensor 206 may be configured to communicatively couple to the one or more processor 110.

Figure 3:
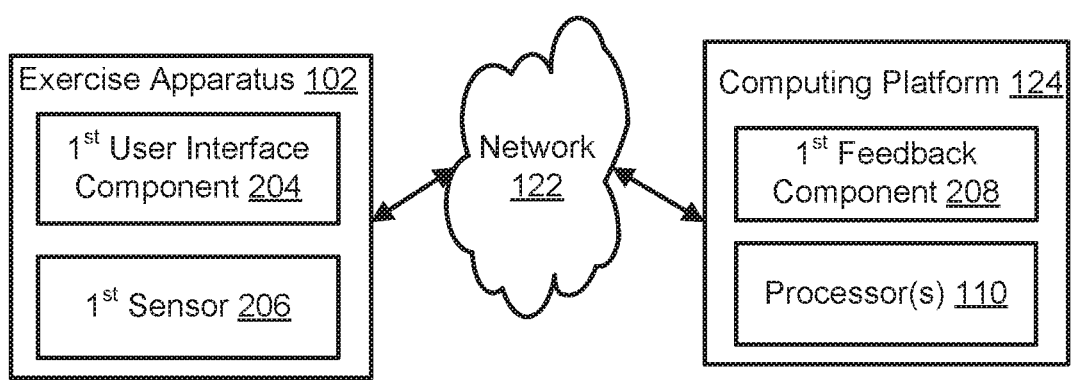
FIG. 3 illustrates another exemplary implementation of an exercise apparatus.

FIG. 3 illustrates another exemplary implementation of an exercise apparatus 102 and/or computing platform 124. The exercise apparatus 102 may include a first user interface component 204, a first sensor 206, and/or other components and/or features. The first sensor 206 may be disposed at the first user interface component 204. A computing platform 124 may include a first feedback component 208, one or more processors 110, and/or other components. The first sensor 206 may be configured to communicatively couple to the one or more processors 110 (e.g., wired or wirelessly). By way of non-limiting example, the first sensor 206 may be configured to communicatively couple to the one or more processors 110 through wireless communications routed through network 122, and/or other communication networks. By way of non-limiting example, the first sensor 206 may be configured to communicatively couple to the one or more processors 110 through wired communications between the first sensor 206 and computing platform 124. In some implementations, the computer platform 124 of FIG. 3 may be configured to communicatively couple with an implementation of exercise apparatus 102 the same or similar to that shown in FIG. 2.

Figure 4:
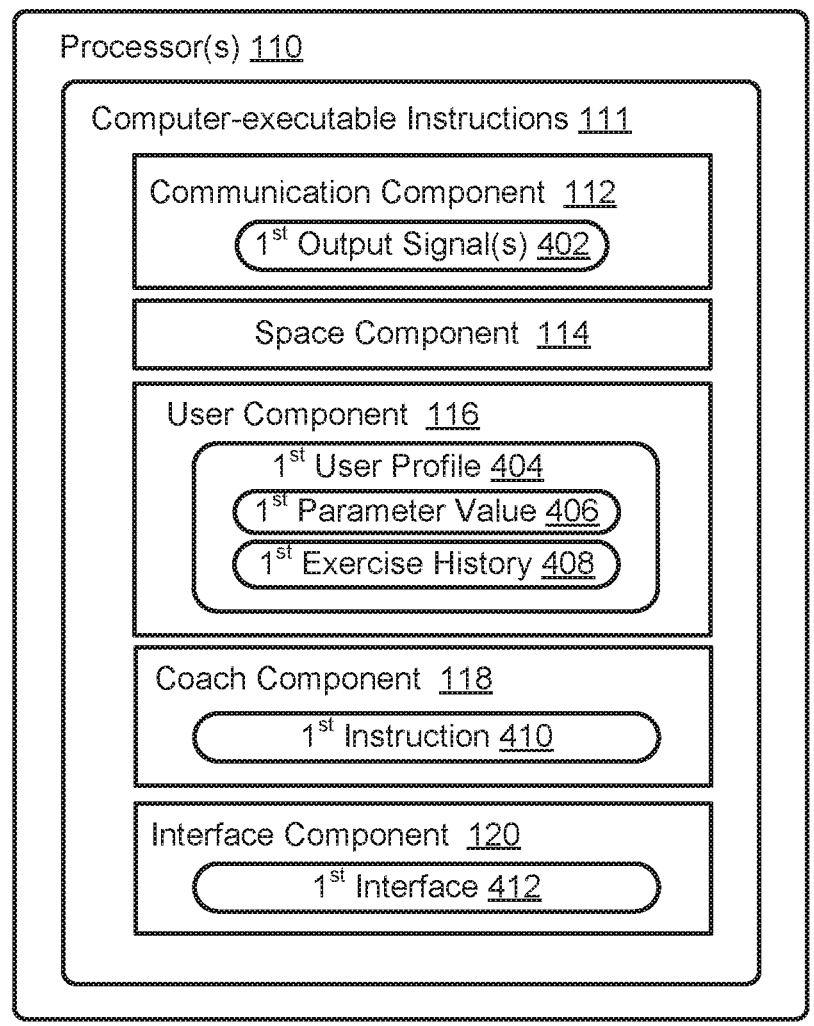
FIG. 4 illustrates one or more processors, in accordance with one or more implementations.

Referring now to FIG. 1 and FIG. 4, the one or more processors 110 may be configured to execute computer-executable instructions 111. The computer-executable instructions 111 may include one or more of a communication component 112, a space component 114, a user component 116, a coach component 118, an interface component 120, and/or other components. It is noted that the following description may refer to implementations wherein the processor(s) 110 may be disposed at one or more of the exercise apparatus 102, a computing platform 124, and/or server 126 (as shown in FIG. 4). In some implementations, the components may be executed by different processors disposed at other locations in system 100.

In FIG. 1, the communication component 112 may be configured to facilitate information communication between computer program components of the processor(s) 110, between one or more computer program components and an entity external to the processor(s) 110 (e.g., a feedback component, a sensor, and/or other entity), and/or may facilitate other information exchange(s). By way of non-limiting example, information communication between two or more computer program components executed by the processor(s) 110 may be routed through the communications component 112, and/or other components. By way of additional non-limiting example, information communicated to and/or from one or more computer program components of the processor(s) 110 and an entity external to the processor(s) 110 may be routed through the communication component 112, and/or other components.

In some implementations, the communication component 112 may be configured to obtain output signals associated with one or more sensors 106 and/or may obtain other information. The communication component 112 may be configured to obtain output signals by virtue of one or both of wired or wireless communications established between the processor(s) 110 (e.g., communication component 112) and one or more sensors 106, and/or over other communication networks. For example, the communications component 112 may be configured to obtain output signals from the one or more sensors 106 directly (or indirectly). As an illustrative example in FIG. 4, the communication component 112 may be configured to obtain first output signal(s) 402.

Returning to FIG. 1, the space component 114 may be configured to execute an instance of a virtual space and/or game and implement the instance of the virtual space and/or game to facilitate user participation in the virtual space and/or a game that takes place in the virtual space. The executed instance of the virtual space may determine the state of the virtual space. The state may then be communicated to a feedback component 108 (e.g., display) for presentation to a user. The state determined and transmitted to a given feedback component 108 may correspond to a view of a game entity being controlled by a user via an exercise apparatus 102 and/or computing platform 124. The state determined and presented to a given feedback component may correspond to a location in the virtual space (e.g., location in the game). The view described by the state presented by the feedback component may correspond, for example, to the location, from which the view is taken, the location the view depicts, and/or other locations, a zoom ratio, a dimensionality of objects, a point-of-view, and/or parameters of the view. One or more of the view parameters may be selectable by the user.

An instance of the virtual space may comprise a simulated space that is accessible by users via a feedback component that presents the views of the virtual space to a user. The simulated space may have a topography, express ongoing real-time interaction by one or more users, and/or include one or more objects positioned within the topography that are capable of locomotion within the topography. In some instances, the topography may be a one-dimensional topography. By way of non-limiting example of a one-dimensional topography, a game mechanic may include one-dimensional motion that is controlled based on force exerted on exercise apparatus 102 (e.g., more force moves avatar to the left and less force moves avatar to the right). In one exemplary implementation, two users may control sumo wrestler avatars that move right or left depending on forces applied by the two users to their respective exercise apparatuses 102 so that the velocity of movement is proportional to the difference in the magnitudes of the forces. A similar control technique may be applied to games involving arm wrestling, track races, and/or other games that incorporate one-dimensional movement and/or topography. In some instances, the topography may be a two-dimensional topography. In some instances, the topography may be a three-dimensional topography. The topography may include dimensions of the space, and/or surface features of a surface or objects that are "native" to the space. In some instances, the topography may describe a surface (e.g., a ground surface) that runs through at least a substantial portion of the space. In some instances, the topography may describe a volume with one or more bodies positioned therein (e.g., a simulation of gravity-deprived space with one or more celestial bodies positioned therein). An instance executed by the computer components may be synchronous, asynchronous, and/or semi-synchronous.

The above description of the manner in which the state of the virtual space is determined by space component 114 is not intended to be limiting. The space component 114 may be configured to express the virtual space in a more limited, or richer, manner. For example, views determined for the virtual space representing the state of the instance of the virtual space may be selected from a limited set of graphics depicting an event in a given place within the virtual space. The views may include additional content (e.g., text, audio, pre-stored video content, and/or other content) that describes particulars of the current state of the place, beyond the relatively generic graphics. For example, a view may include a two-dimensional maze with boundaries/walls/obstacles of which the user must navigate a game entity through to reach an end of the maze. As other examples, a view may include one or more of a skier on a track, sumo wrestlers on a dohyo, arm wrestlers on a table, humans/animals/vehicles on a racing track, and/or other views. Other expressions of individual places within the virtual space are contemplated.

Within the instance(s) of the virtual space executed by space component 114, users may control game entities, simulated physical phenomena (e.g., wind, rain, earthquakes, and/or other phenomena), and/or other elements within the virtual space to interact with the virtual space and/or each other. The game entities may include virtual characters such as avatars. A game entity may be controlled by a user with which it is associated. The user-controlled element(s) may move through and interact with the virtual space (e.g., non-user characters in the virtual space, other objects in the virtual space such as boundaries, obstacles, starting lines, finish lines, and/or other content of a virtual space). Controlling the game entities may include controlling the movement and/or other aspect of the game entities within the virtual space based on control inputs. The user-controlled elements controlled by and/or associated with a given user may be created and/or customized by the given user. The user may have an "inventory" of virtual items and/or currency that the user can use (e.g., by manipulation of a game entity or other user-controlled element, and/or other items) within the virtual space.

The users may participate in the instance of the virtual space by controlling one or more of the available user-controlled game entities in the virtual space. Control may be exercised through control inputs and/or commands input by the users through the exercise apparatus 102, computing platform 124, and/or other input mechanism. In some implementations, one or more values for one or more parameters of muscular activity determined by the user component 116 (described herein), may be provided as control inputs for controlling game entities in the virtual space. Controlling the game entities may include controlling the movement (e.g., positioning) of the game entities within the virtual space.

The users may interact with each other through communications exchanged within the virtual space. Such communications may include one or more of textual chat, instant messages, private messages, voice communications, and/or other communications. Communications may be received and entered by the users via their respective computing platform 124 and/or exercise apparatus 102. Communications may be routed to and from the appropriate users through network 122 and/or through communications which are external to the system 100 (e.g., text messaging services associated with computing platforms 124).

In some implementations, a virtual space and/or game may be executed by a game system 125 comprising one or more processors (not shown) that may be separate from the exercise apparatus 102, computing platforms 124, and/or server 126. For example, a game system 125 may be provided by some external resource 128 and/or other source of information in system 100. However, in some implementations, the game system 125 may be provided as part of the one or more processors 110.

In FIG. 1, the user component 116 may be configured to access and/or manage one or more user profiles and/or user information associated with users. The one or more user profiles and/or user information may include information stored by the exercise apparatus 102, computing platform 124, server 126, and/or other storage locations. The user profiles may include, for example, information identifying users (e.g., a username or handle, a number, an identifier, and/or other identifying information), security login information (e.g., a login code or password), virtual space account information, subscription information, virtual (or real) currency account information (e.g., related to currency held in credit for a user), virtual inventory information (e.g., virtual inventories associated with the users), relationship information (e.g., information related to relationships between users), virtual space usage information (e.g., a login history indicating the frequency and/or amount of times the user logs in to the user accounts and/or participates in a game), information stated by users (e.g., sex, a height, weight, body type, fitness level, body mass index, and/or other information), a computing platform identification associated with a user, a phone number associated with a user, one or more values for parameters of muscular activity associated with the user, an exercise history associated with the user, and/or other information related to user.

In some implementations, the user component 116 may be configured to determine one or more values for one or more parameters of muscular activity associated with the users. The user component 116 may be configured to determine values based on sensor output signals (e.g., obtained from the communications component 112), and/or other information. A value of a given parameter may be numerical (e.g., points, amount, score, rank, ratings, grades, or any other type of numerical expression), descriptive (e.g., text description, and/or other description expression), progressive (e.g., high, medium, low, and/or other progressive expression), pictorial (e.g., an image, a graphic, and/or other visual expression), and/or any other type of expression of a value for a parameter.

In some implementations, the user component 116 may determine values of parameters for the users. A determination may be based on one or more specifications. A specification may include one or more of a function, formula, table, and/or other type of specifications. A given function, formula, table, and/or other type of specification may be stored in electronic storage 121, and/or other storage location. A given function, formula, table, and/or other type of specification may specify that for a given output signal a given value is allocated for a given parameter. By way of non-limiting illustration, a given function, formula, table, and/or other type of specification may specify that for a given output signal that is directly related to a parameter of muscular activity (e.g., a force measurement sensor that generates output signals conveying force amounts and/or a touch sensor that generates output signals conveying a number of instances of contact the sensor), the value becomes the output signal. By way of non-limiting illustration, a given function, formula, table, or any other type of specification may specify that for a given output signal that is indirectly related to a parameter of muscular activity (e.g., a position sensor that generates output signals related to displacement used to calculate force, and/or other indirect relationship), a formula may be applied to the output signal and the result of the applied formula becomes the value, and/or other specification. By way of non-limiting example, a first output signals may become a first value for a first parameter. By way of non-limiting example, the result of a first formula applied to a first output signal may become a first value for a first parameter.

By way of non-limiting example, a parameter of muscular activity may include an exercise parameter corresponding to a given exercise performed by the user. A type of specification (e.g., a table) may specify that for output signals conveying zero displacement of a sensor coupled to a user interface component, and conveying an amount of force being applied to the same user interface component, the value of the exercise parameter may become "isometric exercise," and/or other exercise.

By way of non-limiting example, a parameter of muscular activity may include a muscle activation parameter corresponding to a muscle and/or muscle group activated by a user during performance of a given exercise. A type of specification (e.g., a table) may specify that for output signals conveying that a user is engaging a particular user interface component 104 (by virtue of a sensor being specifically coupled to the user interface component and generating out signals), a value for the muscle activation parameter becomes a description of the muscle and/or muscle group corresponding to a body part of which the given user interface component 104 is configured to engage. For example, a table may store a list of muscles and/or muscle groups associated various body parts of a user, and may correlate these muscle and/or muscle groups with a particular user interface component configured to engage the corresponding body part.

By way of non-limiting example, a parameter of muscular activity may include a force parameter corresponding to an amount of force exerted by a muscle and/or muscle group during a given exercise. A type of specification (e.g., a table) may specify that for output signals conveying information related to an amount of force exerted by a user (either directly or indirectly), a value for the force parameter becomes the output signal (for output signals directly related to force) or a result of a formula being applied to the output signal (for output signals indirectly related to force). In some implementations, formulas may be provided by a provider of the system 100 and/or determined based on the configuration of exercise apparatus and/or user interface components, the material properties of the user interface components, the positioning of the sensors generating the output signals, and/or other aspect.

By way of non-limiting example, a parameter of muscular activity may include a repetition parameter corresponding to an amount of repetitions of activation of the muscle and/or muscle group by a user during a given exercise. A type of specification (e.g., a table) may specify that for output signals conveying information related to the number of repetitions performed by the user (either directly or indirectly), a value for the repetition parameter becomes the output signal (for output signals directly related to repetition), a result of a formula being applied to the output signal (for output signals indirectly related to repetition), and/or other specification. By way of non-limiting example, a touch sensor may generate output signals conveying a count of instances of contact with the sensor (e.g., each instance related to one rep). Individual counts may increase a value for the repetition parameter by one unit. By way of non-limiting example, a force measurement sensor may generate output signals that convey a quantification of force as a continuous or discrete waveform corresponding to an application of force by a user. The waveform may convey information related to an application of force followed by a reduction in an application of force. A transition from application to non-application may correspond to a single rep (e.g., associated with an activation of a muscle or muscle group followed by a relaxation of the muscle and/or muscle group).

By way of non-limiting example, a parameter of muscular activity may include a time parameter corresponding to an elapsed time of performance of a given exercise and/or an elapsed time between repetitions. The user component 116 may be configured to start a time clock responsive to user input conveying they are beginning an exercise (or rep) and/or based on obtaining a first output signals following a powering on of the exercise apparatus 102 and/or one or more physical processors 110. The user component 116 may be configured to stop a time clock responsive to user input conveying that they ended an exercise and/or based on a timeout period of an absence of output signals following reception of an output signal. A timeout period may be one or more seconds, minutes, and/or other time duration. The user component 116 may be configured to determine a value for the time parameter based on time duration between the start and end and/or between the start and end minus the timeout period, and/or other time duration.

By way of non-limiting example, a parameter of muscular activity may include an energy parameter corresponding to an amount of energy expended by the user during a given exercise and/or repetition. Energy expenditure may include calories burned, and/or other measure of energy. A formula or table may be used to determine an amount of energy expended (e.g., average, total, current, and/or other amount) based on one or more of values of other parameters of muscle activity, information about a user (e.g., gender, age, height, weight, body type, fitness level, and/or other information), and/or other information. For example, a formula may be used to determine an amount of calories burned for a person of a given height and/or weight based on an amount of force exerted by a given muscle and/or muscle group and/or other information.

The user component 116 may be configured to determine exercise histories associated with the users. Exercise histories may include historical information associated with the users and/or other information. Historical information may be associated with values for parameters of muscular activity of the users. Historical information may be determined based on the values and/or changes in the values over time. In some implementations, historical information may correspond to one or more aspects of user interaction with an exercise apparatus. By way of non-limiting example, historical information may correspond to user strength, performance, reactivity, control, overall improvement, and/or other information. Historical information may be used to determine one or more ways to improve, areas of improvement, and/or other information. For example, a first exercise history associated with a first user may convey first historical information based on values or changes in values for a first parameter.

In some implementations, historical information determined based on values and/or changes in values may be expressed numerically (e.g., value, points, amount, score, rank, ratings, grades, or any other type of numerical expression), descriptive (e.g., text description, and/or other descriptive expression), progressive (e.g., high, medium, low, and/or other progressive expression), pictorial (e.g., an image, a graphic, and/or other pictorial expression), and/or any other type of expression used to convey historical exercise information. For example, first historical information may be associated with user strength and/or other aspect. The first historical information may be expressed as a first "strength level," "moderately strong," "$1/10$," an image of a bicep of a particular girth, and/or other expressions.

In some implementations, based on values for a parameter meeting one or more threshold values over time (e.g., over a period of one or more exercises), the user component 116 may be configured to update an exercise history of a user to convey the user has reached or obtained a particular exercise state, and/or other perform other operations. For example, if a value for the first parameter meets a first threshold value, the user component 114 may be configured to include second historical information in the first exercise history. The second information may express, for example, a second "strength level," "very strong," "$3/10$," an image of a bicep of a particular girth, and/or other expressions.

In some implementations, historical information may be presented to a user. Historical information may be represented graphically (e.g., a chart, graph, plot, and/or other graphical representation), audibly, textually, and/or other representation. For example, the changes in values for a parameter may be plotted on a graph with respect to time.

In some implementations, based on historical information conveying that a value of a parameter does not meet a threshold, the user component 116 may be configured to determine which aspects of exercise may need improvement. This may include determining that one or more muscles and/or muscle groups need to be improved in terms of strength, control, reactivity, and/or other aspect. For example, based on the first historical information conveying that the value of the first parameter does not meet a first threshold, the user component 116 may be configured to determine that a first muscle and/or muscle group may need improvement.

The above description of user exercise histories is not intended to be limiting. Instead, it is provided for illustrative purposes and should not be limiting with respect to exercise histories, determining historical information from values, presenting historical information to a user, and/or determining ways for improvement based on the historical information. Exercise histories may be determined and/or expressed in other ways.

By way of non-limiting illustration in FIG. 4, the user component 116 may be configured to access and/or manage a first user profile 404 for a first user. The user component 116 may be configured determine a first parameter value 406 for a first parameter of muscular activity associated with the first user profile 404. The user component 116 may be configured to determine a first exercise history 408 associated with the first user profile 404. For example, the first exercise history 408 may be determined based on the first value 406, and/or other information.

In FIG. 1, the coach component 118 may be configured to establish an exercise regime to be performed by a user (e.g., including one or more exercises to be performed), provide exercise instructions and/or other feedback to a user based on an exercise regime (e.g., effectuate an activation or triggering of a feedback component 108), and/or perform more or less functions.

Establishing an exercise regime to be performed by a user may include one or more of calibrating to a particular user, determining one or more exercises to be performed, and/or other operations. Calibration may include determining user information (e.g., user gender, age, height, weight, fitness level, and/or other information), a maximum threshold of force exertion by a user on individual ones of the one or more user interface components 104, and/or other operations. At least some of the user information may be determined from the user component 116.

Determining maximum threshold(s) may be accomplished by a calibration session instructed to the user, and/or other operations. The coach component 118 may be configured to effectuate a calibration session via a feedback component 108 (e.g., a display) and/or other components. A calibration session may comprise instruction to exert a maximum amount of force onto individual ones of the user interface components 104 using the corresponding muscles and/or muscle groups, or combinations of user interface components 104 by the user. A calibration session may comprise instruction to assume a pose while exerting a force onto individual ones of the user interface components 104 using the corresponding muscles and/or muscle groups, or combinations of user interface components 104 by the user. The communication component 112 may be configured to receive sensor output signals during the calibration session. The user component 116 may be configured to determine values for a force parameter or other parameter associated with individual ones of the user interface components 104 based on the sensor output signals, and/or may associate the values to a muscle and/or muscle group activated by the user according to a corresponding user interface component 104. The user component 116 may be configured to store these determined values as "maximum threshold" force values associated with a corresponding user interface component 104 and/or muscle and/or muscle group of a user. Calibration may include other operations.

Determining one or more exercises to be performed by a user may be accomplished in a variety of ways. In some implementations, an exercise to be performed by a user may be determined based on user entry and/or selection via a feedback component 108 and/or computing platform 124 specifying a desired exercise. In some implementations, an exercise to be performed by a user may be determined simply by the user performing a given exercise. In some implementations, determining one or more exercises to be performed by a user may be based on exercise histories associated with the users. In some implementations, determining one or more exercises to be performed by a user may be based on a calibration session (e.g., the maximum threshold values). For example, the coach component 118 may be configured to store a list or table of various exercises that may be performed to increase strength, power, agility, control, and/or other aspect of a muscle and/or muscle group. The coach component 118 may be configured to store a list or table of typical or "average" or target maximum threshold forces for an individual of a given weight, height, fitness level (e.g., determined based on statistical analysis of individuals, such as a $50^{th}$ percentile average, $60^{th}$ percentile average, and/or other information). The coach component 118 may be configured to compare the maximum threshold values (and/or values associated with the exercise histories) for a given user and compare these values to those in the list or table of target values. Based on the comparison, the coach component 118 may be configured to determine individual ones of the values that may be less than a corresponding average value. The coach component 118 may be configured to determine one or more exercises to be performed by a user in order to bring the value(s) up to the target (e.g., over time by performing one or more select exercises). Other ways in which exercises may be determined for a user are also contemplated.

The coach component 118 may be configured to effectuate presentation of exercise instruction via one or more feedback components 108 prior to, during, and/or after an exercise. Effectuating presentation of exercise instruction via one or more feedback components 108 may include sending one or more activation and/or triggering signals or messages (e.g., via communication component 112) to a given feedback component 108.

In some implementations, instruction may be related to coaching the user on exerting forces on the one or more user interface components 104. The instruction may be related to coaching the user to activate one or more muscles and/or muscle groups. The instruction may be related to coaching the user to exert a predefined amount of force. The instruction may be related to coaching the user to exert a percentage of their maximum threshold force. The instruction may be related to coaching the user to exert a force for a predefined amount of time. The instruction may be related to coaching the user to exert a force for a predefined number of repetitions. The instruction may be related to any combination of instructions as described herein.

In some implementations, instruction may include feedback related to coaching a user during a currently preformed exercise, providing instructions on how to perform one or more subsequent exercises, providing feedback on a previously performed exercise, and/or other feedback. Instructional feedback may include feedback on how to use a select muscle and/or muscle group, how to engage one or more user interface components 104, encouraging feedback, corrective feedback, neutral feedback, and/or other feedback. By way of non-limiting example, such instructional feedback may be related to a number of reps a user should do, an amount of force (or change in an amount of force) a user should impart during a rep, a frequency of performance of a rep, an amount of time a user should perform one or more exercises and/or reps, an indication to change a select muscle and/or muscle/group being activated to a different muscle and/or muscle group, and/or other instruction. In some implementations, instructional feedback may be provided in real time as the user is performing an exercise and/or rep, prior to the user starting to perform an exercise and/or rep, after an exercise or rep is performed, and/or at other times.

In some implementations, instructional feedback may include instruction that a given user interface component 104 should be engaged by a user, that a given muscle and/or muscle group should be activated by the user with a given user interface component 104, and/or other instruction. One or more of visual feedback, auditory feedback, tactile feedback, olfactory feedback, and/or other feedback may facilitate indicating to a user which user interface component 104 to engage and/or muscle and/or muscle group to activate. For example, a first feedback component may be activated and/or trigger to provide first instructional feedback to a user.

By way of non-limiting example, a given feedback component 108 (e.g., a vibrator, a heating element, a light source, a scent apparatus, a display, a speaker, and/or other feedback component) coupled to a given user interface component 104 configured to engage a given body part of a user, may be activated and/or triggered (e.g., may vibrate, heat up/cool down, emit light, emit a scent, display an image, graphic and/or text, alert a sound, and/or other feedback) to indicate that the corresponding user interface component 104 should be engaged using the corresponding body part. By way of additional non-limiting example, a feedback component 108 may be activated a certain number of times to indicate a certain number of repetitions of muscle and/or muscle group activation should be performed with the given user interface component 104. In some implementations, the triggering and/or activation of a feedback component 108 may be achieved by the one or more physical processors 110, described herein.

In some implementations, feedback may include feedback that responds to user activity and/or user interaction with the user interface component 104 during a currently preformed exercise, and/or other feedback. Feedback responding to user activity and/or interaction may include activation of one or more feedback components 108 based on a sensor output received from one or more sensors 106 indicating particular action or activity by the user, and/or other aspect of user interaction. For example, responsive to reception of a first output signal (e.g., by the one or more physical processors 110), a first feedback component may be triggered/activated.

By way of non-limiting example, if a user is instructed to engage a given user interface component 104, responsive to one or more sensors 106 generating output signals related to the user contacting the given user interface component 104, one or more feedback components 108 may be activated to indicate the user has successfully followed the instructions. By way of additional non-limiting example, if a user is instructed to exert a given amount of force on a given user interface component 104, responsive to one or more sensors 106 generating output signals related to the user contacting the given user interface component 104 and exerting the instructed amount of force (e.g., based on the output signals being used to determine a value for a force parameter), one or more feedback components 108 may be activated to indicate the user has successfully followed the instructions. In some implementations, feedback may be provided that may indicate a user has unsuccessfully followed instructions.

By way of non-limiting example as to the evolution of instructional feedback being provided to a user, the coaching component 118 may be configured to effectuate presentation of exercise instruction via a feedback component 108. The communication component 112 may be configured to obtain output signals from one or more sensors coupled to one or more user interface components 104 of an exercise apparatus 102. The user component 116 may be configured to determine values for the one or more parameters of muscular activity based on the output signals. The coach component 118 may be configured to modify the presented exercise instruction based on the determined values. For example, if the determined values indicate that the user successfully followed instructions for a given exercise, the instruction may be changed to instruct the user to perform one or more other exercises, and/or other actions and/or activities. As another example, if the determined values indicate that the user has not successfully followed instructions for a given exercise, the instruction may be changed to instruct the user to perform the same exercise again or in a different manner, perform one or more different exercises, and/or other instruction. In some implementations, the modification may correspond to coaching the user to continue exerting forces using a given muscle and/or muscle group, to exert forces using a different muscle and/or muscle group, and/or other modification. In some implementations, the modification may include presenting different instructional feedback.

The above description of the manner in which feedback may be provided to a user via a feedback component 108 is not intended to be limiting. One or more feedback components 108 may be configured to effectuate visual feedback, auditory feedback, tactile feedback, olfactory feedback, and/or other feedback in a more limited, or richer, manner. By way of non-limiting example, instructional information displayed on a screen may be selected from a set of graphics or text conveying to the user a particular exercise to perform, user interface component 104 to engage, muscle and/or muscle group to activate, and/or other information. The displayed information may be accompanied by additional content (e.g., audio, pre-stored video, scents, vibrations, sounds, light emissions, and/or other content) that describes one or more aspects of exercise and/or user performance that go beyond the graphics and/or text. For example, a view displayed on a display screen may include a generic textual description of a given user interface component 104 the user should engage and/or an amount of force the user should try to impart on the given user interface component 104; a vibrator coupled to the given user interface component 104 may simultaneously be activated; a scent may be emitted in response to the user engaging the appropriate given user interface component 104 (e.g., based on sensor output indicating a contact of the user interface component 104 by the user, and/or other sensor output); and/or more or less feedback may be provided. Other ways in which feedback and/or combinations of feedback may be presented to a user are contemplated.

By way of non-limiting illustration in FIG. 4, the coach component 118 may be configured to effectuation presentation of first instruction 410 to the first user via a first feedback component (not shown in FIG. 4).

Returning to FIG. 1, in some implementations, interface component 120 may be configured to effectuate presentation of an interface via a feedback component 108 (e.g., a display/screen). The interface component 120 may be configured to effectuate presentation of views of a virtual space and/or game executed by the space component 114. The interface component 120 may be configured to effectuate presentation of an interface including one or more of: a portion conveying a view of a game taking place in a virtual space executed by the space component 114, the game including a game entity controlled by a user and/or other virtual space content; a game control element configured to receive user entry and/or selection to control one or more aspects of gameplay; a portion conveying information related to control inputs for controlling a game entity in a game space; a portion conveying information related to values for one or more parameter of muscle activity associated with a user; and/or other portions.

Figure 5:
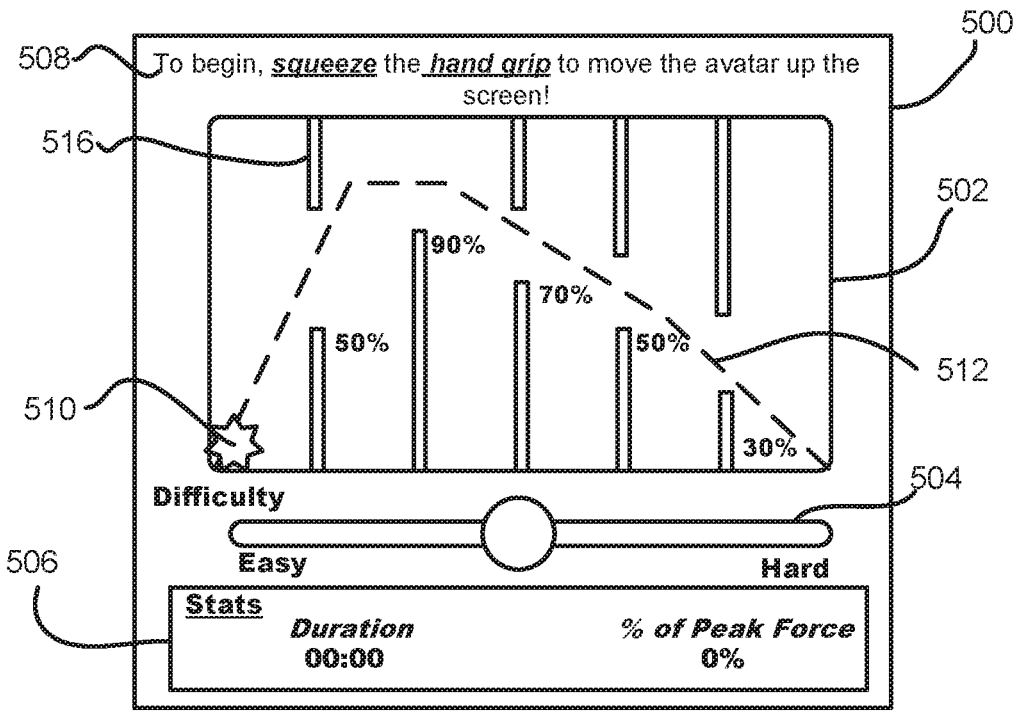
FIG. 5 illustrates an exemplary implementation of a user interface for gaming.
Figure 6:
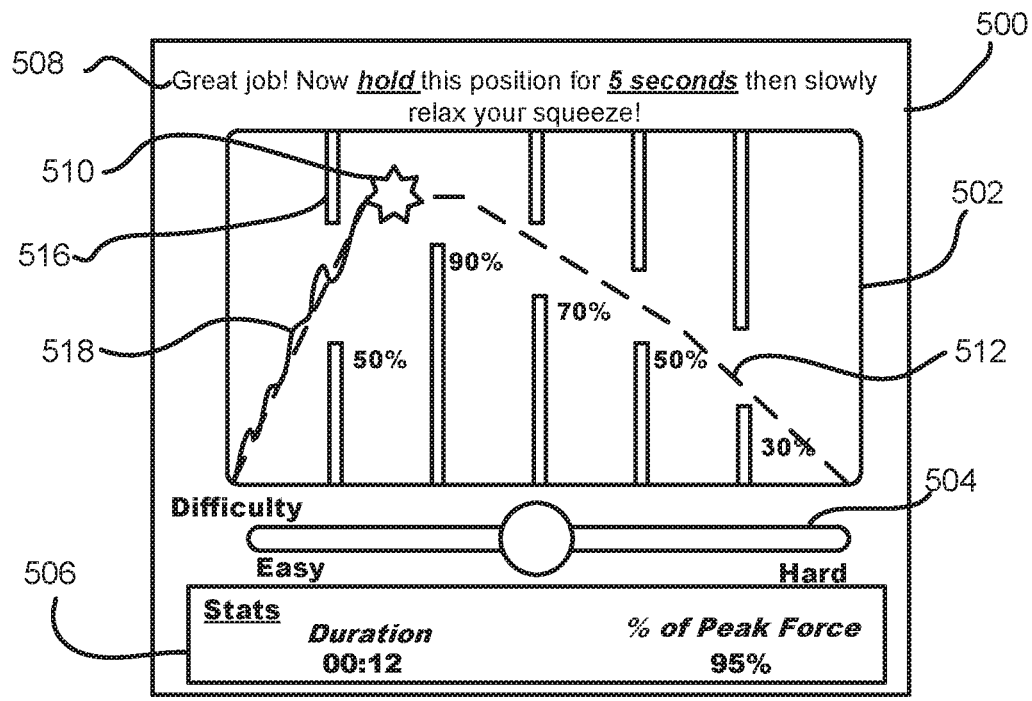
FIG. 6 illustrates another exemplary implementation of a user interface for gaming.

By way of non-limiting illustration in FIG. 5 and FIG. 6, an implementation of an interface 500 for gaming is depicted. The interface 500 may include one or more interface elements and/or portions. The interface elements and/or portions may comprise one or more of: a gameplay portion 502 including a game entity 510 associated with a user, and gameplay elements such as a path 512 and obstacles 516; a control element 504 for controlling one or more aspects of gameplay; an information display portion 506 configured to display gameplay information; an instruction portion 508 configured to display exercise instructions; and/or other portions and/or elements. The depiction of interface 500 in FIGS. 5 and 6 is not intended to be limiting as interface 500 may include more or less elements than is shown. For example, in some implementations, one or more elements may be omitted from interface 500. As another example, the functionality described in connection with two or more elements may be combined as a single element.

In some implementations, the gameplay portion 502 may represent a graph showing magnitude of the force (e.g., y-axis) that the user is expected to exert over time (e.g., x-axis). The path 512 (e.g., dashed line) may be the target force curve that the user has to follow over time. The width of the openings in the obstacles 516 (e.g., vertical bars) may determine the tolerance around the target curve where the performance is considered correct. The horizontal density of the vertical bars may determine the number of control points where performance precision is evaluated. The farther from the opening the game entity 510 (e.g., star) crosses the bar, the less precision may be recorded. The horizontal density and the opening width of the bars may be controlled with the control element 504 (e.g., difficulty slider)—more difficulty may be more bars and narrower openings, which may force the user to be much closer to the target curve. The user may be awarded different amounts of award points depending on the difficulty level chosen and precision achieved during execution. The information display portion 506 may be configured to enable the user to change the overall duration of the exercise repetition and/or to change the value of the highest point on the curve, as percentage of the calibrated force for the specific pose. Changing peak force may result in stretching the curve vertically. In some implementations, the user can may change the pose, the number of repetitions, the rest between repetitions, and/or other aspects of the exercise. In some implementations, the game entity 510 may represent the current force value. The game entity 510 may move with even velocity left to right as repetition time runs. Meanwhile the game entity 510 may also move vertically with variable velocity, depending on the changes in the exerted force.

In some implementations, a graphical "skin" may be applied to the interface 500. For example, the interface 500 may be depicted such that the path 512 may be a ski track, the openings between opposing obstacles 516 may be shown as poles, and the obstacles 516 may be replaced with obstacles of different types (e.g., rocks, pine trees, and/or other types). For graphical relevance, the interface 500 may be rotated 90 degrees. The game entity 510 may be depicted as a skier moving down. More force may move the skier right while less force may move the skier left.

In some implementations, the user may be instructed to move the game entity 510 through a maze comprising the path 512, obstacles 516, and/or other elements. The path 512 may be associated with moving the game entity 510 over the obstacles 516 and across the screen (e.g., in the current depiction, from left to right). At the start of gameplay, the game entity 510 may automatically begin moving horizontally across the screen. This may be similar to a type of "side scrolling" game, and/or other game. However, in some implementations, control inputs may be provided by a user which may determine an amount of horizontal movement of the game entity 510. In some implementations, the user may provide inputs in a manner to maneuver the game entity 510 vertically in the game to overcome the obstacles 516 and successfully move the game entity 510 to the other end of the maze. In some implementations, the control inputs for controlling a vertical position of the game entity 510 may be associated with user interaction with user interface components of an exercise apparatus. By way of non-limiting example, by exerting a force (e.g., squeezing) on a user interface component using a body part (e.g., their hands) output signals from one or more sensors may be generated. The output signals may be used to determine values for a force parameter and/or other parameter. The values may be provided as control inputs to move the game entity 510 vertically, and/or in other directions. For example, a quantification of force may correspond to an amount of movement of the game entity 510.

In some implementations, traversing an obstacle 516 may include exerting an amount of force required to move the game entity 510 to an appropriate position. The requisite amount may be provided to the user via instruction 508 presented to the user. The requisite amount may be shown in the gameplay portion 502. For example, adjacent each obstacle 516 may include a maximum threshold percentage amount required to appropriately position the game entity 510 to traverse the obstacles 516.

The control element 504 may facilitate controlling one or more aspects of gameplay. In the current figure, difficulty may comprise at least one of the aspects of gameplay that may be controlled. Other aspects may include a size of the maze, a type of game (e.g., race game, and/or other game), and/or other aspects. Other aspects are also contemplated. By way of non-limiting example, the control element 504 may comprise a sliding indicator which may allow a user to change a difficulty (or other aspect) between relatively easier to relatively harder. In some implementations, an "easy" game may be associated with less force required to overcome obstacles 516; the game entity 510 moving slower across the screen; and/or other game aspects. A relatively "harder" game may require more force and/or the game entity 510 may move faster, and/or other game aspects may be different. It is noted that the control element 504 may be any type of element configured to receive user entry and/or selection. For example, control element 504 may be a drop-down menu presenting a list of selectable options, a series of check boxes of which the user may select as desired, and/or other control element.

Information display portion 506 may be configured to display gameplay information and/or other information. Gameplay information may include one or more of a current state of control inputs provided by the user (e.g., a current percentage of maximum force exerted by the user and/or other information), a time clock, and/or other information.

The instruction portion 508 may be configured to display exercise instructions as part of the gameplay experienced by a user. The exercise instruction 508 may be related to gameplay, one or more exercises, and/or other instruction. As such, the presentation of exercise instruction and gaming may be seamlessly integrated.

FIG. 6 illustrates an implementation of gameplay by a user. Gameplay may correspond to controlling the game entity 510 in the virtual space. The movement of the game entity 510 may be represented by a trail 518 corresponding to the real time control inputs provided by the user over time.

In some implementations, gameplay may include multiplayer gameplay, and/or other gameplay. For example, a game may be executed which includes a gaming space, including a first game entity associated with a first user and a second game entity associated with a second user. Views of the game may be presented to the users on a common screen (if they are proximate each other) or on separate displays associated with the users, respectively. The users may then "battle" by controlling the respective game entities using control inputs derived from forces imparted on respective exercise apparatuses associated with the users to achieve a game objective (e.g., complete a maze, and/or other objective).

It is noted that the above description of gameplay using control input determined from sensor output generated during user interaction with an exercise apparatus is not intended to be limiting. Instead, this is provided as an illustrative example and is not intended to limit the way in which control inputs may be provided, a game entity may be controlled, the manner in which gameplay may commence, and/or other aspects related to gaming using an exercise apparatus in accordance with one or more implementations presented herein.

Figure 7:
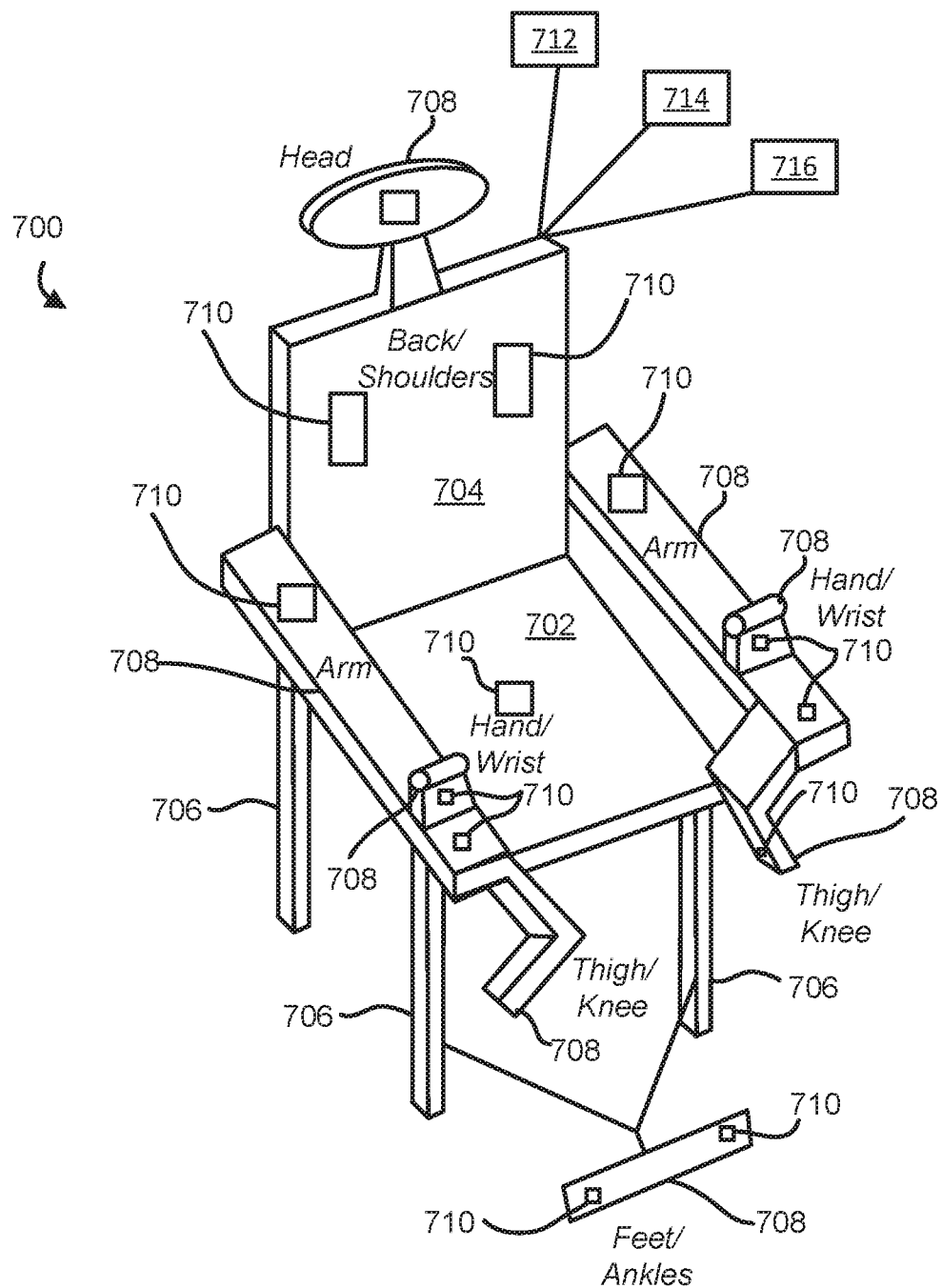
FIG. 7 illustrates an exemplary implementation of an exercise apparatus.

FIG. 7 depicts an implementation of an exercise apparatus 700. Exercise apparatus 700 may be configured to engage a user in a substantially seated position and/or other position (e.g., squatting, supine, prone, crouched, and/or other position). In some implementations, the exercise apparatus 700 may comprise at least part of a chair, stool, bench, tabletop, and/or other structure configured to engage a user in a substantially seated position. In some implementations, at least a portion of the exercise apparatus 700 may be configured and/or designed the same as or similar to co-pending U.S. Design patent application Ser. No. 29/513,417 filed on Dec. 30, 2015 and entitled "Sculpted Chair Arms," which is incorporated herein in its entirety by reference. In some implementations, exercise apparatus 700 may include one or more components of exercise apparatus 102 (see, e.g., FIG. 1).

The exercise apparatus 700 may include one or more user interface components 708 configured to engage one or more body parts of a user, one or more sensors 710, and/or other components. Individual ones of the one or more sensors 710 may be coupled to corresponding individual ones of the one or more user interface components 708. For example, a first sensor 710 may be coupled to a corresponding first user interface component 708. The exercise apparatus 700 may include a feedback component 712, one or more processors 714, a power source 716, and/or other components.

In some implementations, the power source 716 may comprise a battery pack, an electrical cord for connection with a conventional power outlet, a power generating apparatus, and/or other components. A power generating apparatus may comprise, for example, a piezoelectric power generating apparatus. In some implementations, at least a portion of the exercise apparatus 700 may comprise piezoelectric power generating material. For example, piezoelectric power-generating material may be incorporated into a seat 702 of the apparatus 700 to generate power each time a user sits and/or moves upon the seat 702.

In some implementations, the exercise apparatus 700 may include a seat 702, a back support 704, one or more legs/supports 706, and/or other components configured to facilitate engaging a user in a substantially seated position. The user interface components 708 may include components configured and/or arranged to engage one or more of a hand, a wrist, an elbow, an arm, a torso, a head, a shoulder, a back, a hip, a thigh, a knee, a calf, an ankle, a foot, and/or other body part of a user. For example, a first user interface component 708 may be configured and/or arranged to engage a first body part of a user.

By way of non-limiting example, a given user interface component 708 may be configured and/or arranged to engage an arm of a user; a given user interface component 708 may be configured and/or arranged to engage a hand (and/or one or more fingers and/or wrist) of a user; a given user interface component 708 may be configured and/or arranged to engage the back of a user; a given user interface component 708 may be configured and/or arranged to engage a shoulder of a user; a given user interface component 708 may be configured and/or arranged to engage a head (and/or neck) of a user; a given user interface component 708 may be configured and/or arranged to engage a thigh of a user; a given user interface component 708 may be configured and/or arranged to engage a knee of a user; a given user interface component 708 may be configured and/or arranged to engage a leg of a user; a given user interface component 708 may be configured and/or arranged to engage a foot of a user; a given user interface component 708 may be configured and/or arranged to engage an ankle of a user; and/or one or more other user interface components 708 may be configured to engaged any other body of a user.

In some implementations, a user interface component 708 configured to engage a hand (and/or wrist and/or one or more fingers) may comprise a hand grip. The grip may be coupled to a sensor 710. The sensor 710 at the hand grip may be configured to generate output signals conveying information related to an amount of squeezing force exerted by a hand of a user. A user interface component 708 configured to engage an arm of a user may comprise an arm rest. The arm rest may be coupled to one or more sensors 710. A sensor 710 coupled to the arm rest may comprise a sensor configured to measure force. The sensor may be disposed at or near a portion of the arm rest where a user's elbow may lay such that the sensor may generate output signals related to forces exerted via an elbow of the user. A sensor 710 coupled to the arm rest may comprise a sensor configured to measure displacement and may be disposed at a distal end of the arm rest. In some implementations, the back support 704 may be a user interface component 708. The back support 704 may be coupled to one or more sensors 710. For example, one or more sensors configured to measure force may be disposed at one or more locations on the back support that may align with a user's shoulders and/or shoulder blades. A user interface component 708 configured to engage a head of a user may comprise a headrest. As shown, a head rest may be coupled to the back support 704. The head rest may be coupled to one or more sensors 708 configured to measure force exerted by the head or neck muscles of a user. A user interface component 708 configured to engage a thigh/knee of a user may include a thigh/knee portion. The thigh/knee portion may include at least one surface configured to engage a thigh and/or knee of a user while in a substantially seated position. The thigh/knee portion may extend from a distal end of the arm rest, and/or may be configured in other ways. The thigh/knee portion may be coupled to one or more sensors 710 configured to measure force exerted by a user via their thigh and/or knee. A user interface component 708 configured to engage a foot of a user may include a foot rest. The foot rest may include at least one surface configured to engage a foot and/or ankle of a user while in a substantially seated position. The foot rest may be coupled to one or more sensors 710 configured to measure force exerted by a user via their foot and/or ankle.

FIG. 8, FIG. 8a, and FIG. 9 depict an implementation of an exercise apparatus 800. The exercise apparatus 800 may comprise a thin, flexible material defined by a first surface 802, a second surface 804 facing opposite the first surface 802, and a peripheral side edge 806 communicating between the first surface 802 and second surface 804. First surface 802 and/or second surface 804 may be continuous or discontinuous. For example, the exercise apparatus 800 may comprise a sheet, net, web, tarp, cover, coverlet, and/or other thin, flexible material. The exercise apparatus 800 may be formed from fabric, cloth, plastic, leather, and/or other material. The peripheral side edge 806 may define a thickness. In some implementations, the thickness may be in the range of 0-2 cm. In some implementations, the thickness may be in the range of a 0-5 mm. Although the exercise apparatus 800 is shown having a substantially rectangular shape, this for illustrative purposes only and should not be considered limiting. For example, in other implementations, the shape of the exercise apparatus 800 may be circular, oval, square, body shaped, and/or other shape.

The exercise apparatus 800 may include one or more user interface components 808 configured to engage one or more body parts of a user, one or more feedback components 816, one or more processors 818, a power source 820, and/or other components. In some implementations, exercise apparatus 800 may include one or more components of exercise apparatus 102 (see, e.g., FIG. 1). The user interface components 808 may comprise repositionable sensor configurations including one or more sensors 810. For example, a sensor configuration may comprise a sensor bar or pad formed from fabric, foam, and/or other material that houses one or more sensors 810. The sensors 810 may be wireless sensors, wired sensors, and/or other sensors.

One or more user interface components 808 may be movable/repositionable relative to the exercise apparatus 800, or stationary. For example, a given user interface component 808 may be repositionable based on a movable engagement of the user interface component 808 to the exercise apparatus 800. Movable engagement may be provided in a variety of ways. In some implementations, movable engagement may be provided by one or more tracks 812 used to engage a user interface component 808 in a movable engagement. As shown in the illustration of FIG. 8a, a movable engagement may be provided by one or more collars 814 coupled to a given user interface component 808. A collar 814 may be coupled to the user interface component 808 by a fastener such as sewing, rivets, adhesive, and/or other fastener. The collar 814 may be engaged over a track 812 such that the track 812 communicates through a passage of the collar 814. The configuration of the passage may impart an amount of friction onto the track 812. The ends 813 of the track 812 may be fastened to the exercise apparatus 800 (e.g., the first surface 802) via a fastener such as sewing, rivets, adhesive, and/or other fastener. The tracks 812 may be formed from a strip of material such as fabric, plastic, and/or other material. A given repositionable user interface component 808 may be movable along a corresponding track 812 with which it is movably engaged. However, other techniques in which the user interface components 808 may be repositionable and/or movable relative to the exercise apparatus 800 are also contemplated.

In some implementations, one or more user interface components 808 may be removably engageable to the exercise apparatus 800 (e.g., to the first surface 802). Removable engagement of a user interface component 808 to the exercise apparatus 800 may be accomplished by one or more removable fasteners connecting the user interface components 808 to the exercise apparatus 800 (e.g., the first surface 802). A removable fastener may comprise hook and loop fabric (e.g., hood fabric disposed at the first surface 802 and/or loop fabric disposed at the user interface components 808, or vis versa), snap fits, and/or other removable fastener.

In some implementations, the exercise apparatus 800 may comprise flexible material that facilitates covering (e.g., placing over, draping over, and/or other type of covering) a structure with the apparatus 800. For example the exercise apparatus 800 may be configured to cover one or more of a floor, a chair, a stool, a car seat, a bench, a bed, a wall (e.g., be hung on the wall, and/or other positioning), and/or other structure. The user may be able to perform one or more exercises while the exercise apparatus 800 may be covering a structure.

In FIG. 1, the exercise apparatus 102, processor(s) 110, sensor(s) 106, feedback component(s) 108, computing platform(s) 124, game system 125, server 126, and/or external resources 128 may be operatively linked via one or more electronic communication links. For example, such electronic communication links may be established, at least in part, via a network 122 such as a local area network, a wide area network (e.g., the Internet), a short range communication network (e.g., Bluetooth, near-field communication, infrared, and/or other short range network), a wired network (e.g., ethernet, USB, firewire, and/or other wired network), and/or other networks. It will be appreciated that this is not intended to be limiting, and that the scope of this disclosure includes implementations in which exercise apparatus 102, processor(s) 110, sensor(s) 106, feedback component(s) 108, computing platform(s) 124, game system 125, server 126, and/or external resources 128, may be operatively linked via some other communication media.

The external resources 128 may include sources of information, hosts and/or providers of information outside of system 100, external entities participating with system 100, and/or other resources. In some implementations, some or all of the functionality attributed herein to external resources 128 may be provided by resources included in system 100.

The exercise apparatus 102, computing platform(s) 124, game system 125, and/or server 126 may include electronic storage 121, one or more processors 110, and/or other components. The exercise apparatus 102, computing platform(s) 124, game system 125, and/or server 126 may include communication lines or ports to enable the exchange of information with a network and/or other computing platforms. Illustration of exercise apparatus 102, computing platform(s) 124, game system 125, and/or server 126 in FIG. 1 is not intended to be limiting. The exercise apparatus 102, computing platform(s) 124, game system 125, and/or server 126 may include a plurality of hardware, software, and/or firmware components operating together to provide the functionality attributed herein to the exercise apparatus 102, computing platform(s) 124, and/or server 126, respectively.

Electronic storage 121 may comprise electronic storage media that electronically stores information. The electronic storage media of electronic storage 121 may include one or both of system storage that is provided integrally (i.e., substantially non-removable) with exercise apparatus 102, computing platform(s) 124, and/or server 126 and/or removable storage that is removably connectable to exercise apparatus 102, computing platform(s) 124, and/or server 126 via, for example, a port or a drive. A port may include a USB port, a firewire port, and/or other port. A drive may include a disk drive and/or other drive. Electronic storage 121 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storage 121 may include one or more virtual storage resources (e.g., cloud storage, a virtual private network, and/or other virtual storage resources). Electronic storage 121 may store software algorithms, information determined by processor(s) 110, information received from one or more of exercise apparatus 102, computing platform(s) 124, and/or server 126, and/or other information that enables exercise apparatus 102, computing platform(s) 124, and/or server 126 to function as described herein.

Processor(s) 110 is configured to provide information-processing capabilities in exercise apparatus 102, computing platform(s) 124, and/or server 126. As such, processor 110 may include one or more of a digital processor, an analog processor, a digital circuit designed to process information, an analog circuit designed to process information, a state machine, and/or other mechanisms for electronically processing information. Although processor 110 is shown in FIG. 1 as a single entity, this is for illustrative purposes only. In some implementations, processor 110 may include one or more components. These components may be physically located within the same device, or processor 110 may represent processing functionality of a plurality of devices operating in coordination.

The processor 110 may be configured to execute components 112, 114, 116, 118, and/or 120. Processor 110 may be configured to execute components 112, 114, 116, 118, and/or 120 by software; hardware; firmware; some combination of software, hardware, and/or firmware; and/or other mechanisms for configuring processing capabilities on processor 110.

It should be appreciated that, although components 112, 114, 116, 118, and/or 120 are illustrated in FIG. 1 as being co-located within a single component, in implementations in which processor 110 includes multiple components, one or more of components 112, 114, 116, 118, and/or 120 may be located remotely from the other components. The description of the functionality provided by the different components 112, 114, 116, 118, and/or 120 described above is for illustrative purposes and is not intended to be limiting, as any of components 112, 114, 116, 118, and/or 120 may provide more or less functionality than is described. For example, one or more of components 112, 114, 116, 118, and/or 120 may be eliminated, and some or all of its functionality may be provided by other ones of components 112, 114, 116, 118, 120, and/or other components. As another example, processor 110 may be configured to execute one or more additional components that may perform some or all of the functionality attributed to one of components 112, 114, 116, 118, and/or 120.

Figure 10:
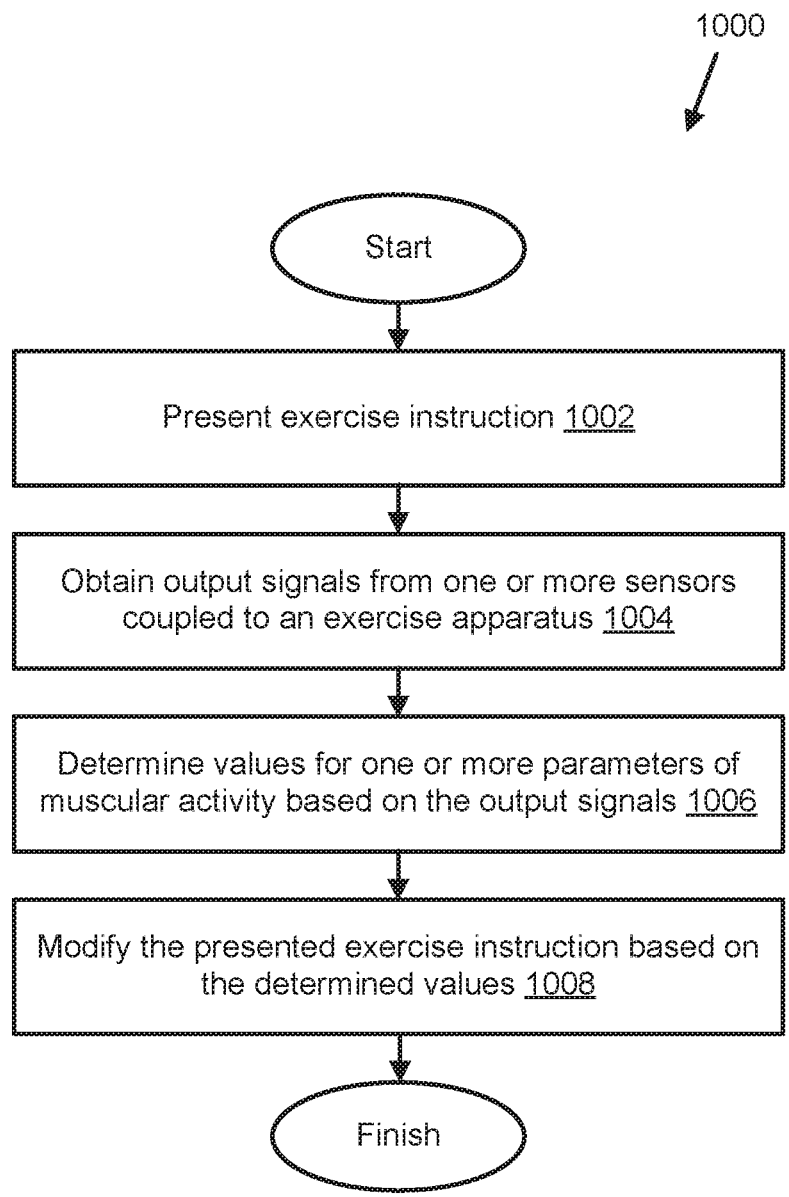
FIG. 10 illustrates a method of coaching a user performing one or more exercises, in accordance with one or more implementations.

FIG. 10 illustrates a method 1000 of coaching a user performing one or more exercises. The operations of method 1000 presented below are intended to be illustrative. In some embodiments, method 1000 may be accomplished with one or more additional operations not described, and/or without one or more of the operations discussed. Additionally, the order in which the operations of method 1000 are illustrated in FIG. 10 and described below is not intended to be limiting.

In some embodiments, method 1000 may be implemented in one or more processing devices (e.g., a digital processor, an analog processor, a digital circuit designed to process information, an analog circuit designed to process information, a state machine, a functionally limited processing device, and/or other mechanisms for electronically processing information). The one or more processing devices may include one or more devices executing some or all of the operations of method 1000 in response to instructions stored electronically on an electronic storage medium. The one or more processing devices may include one or more devices configured through hardware, firmware, and/or software to be specifically designed for execution of one or more of the operations of method 1000.

Referring now to method 1000 in FIG. 10, at an operation 1002, presentation of exercise instruction may be effectuated. The instruction may relate to coaching a user on exerting forces on an exercise apparatus using one or more muscles and/or muscle groups in accordance with one or more exercises. In some implementations, operation 1002 may be performed by a coach component the same as or similar to coach component 118 (shown in FIG. 1 and described herein).

At an operation 1004, output signals from one or more sensors coupled to the exercise apparatus may be obtained. The output signals may convey information related to one or more parameters of muscular activity of the user during the exercises. In some implementations, operation 1004 may be performed by a communication component the same as or similar to the communication component 112 (shown in FIG. 1 and described herein).

At an operation 1006 values for the one or more parameters of muscular activity may be determined based on the output signals. The parameters may correspond to one or more of a muscle and/or muscle group activated by the user during performance of the given exercise, an amount of force exerted by the muscle and/or muscle group during the given exercise, an amount of repetitions of activation of the muscle and/or muscle group, an elapsed time of performance of the given exercise, an amount of calories burned, and/or other aspects of muscular activity. In some implementations, operation 1006 may be performed by a user component the same as or similar to the user component 116 (shown in FIG. 1 and described herein).

At an operation 1008, modification of the presented exercise instruction may be effectuated based on the determined values. The modification may correspond to coaching the user to continue exerting forces using a given muscle and/or muscle group or to exert forces using a different muscle and/or muscle group. In some implementations, operation 1008 may be performed by a coach component the same as or similar to coach component 118 (shown in FIG. 1 and described herein).

Figure 11:
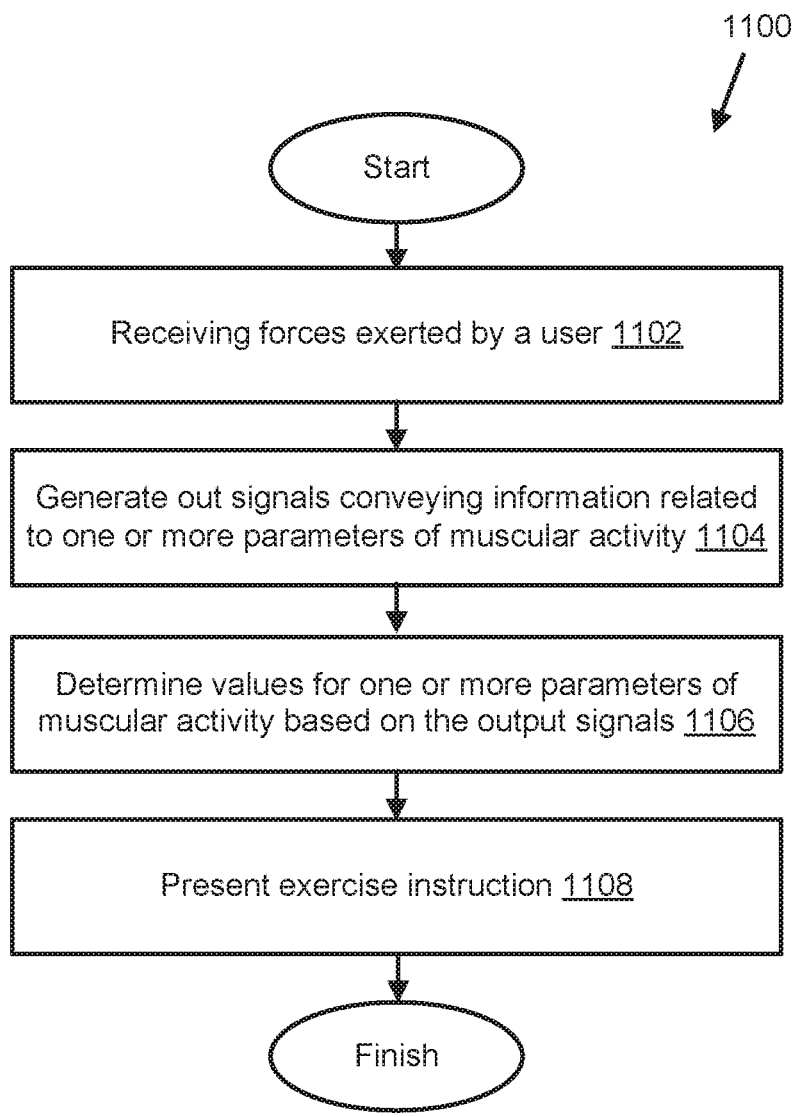
FIG. 11 illustrates a method of evaluating muscular activity of a user during exercise and/or providing feedback to the user, in accordance with one or more implementations.

FIG. 11 illustrates a method 1100 of evaluating muscular activity of a user during exercise and/or providing feedback to the user. The operations of method 1100 presented below are intended to be illustrative. In some embodiments, method 1100 may be accomplished with one or more additional operations not described, and/or without one or more of the operations discussed. Additionally, the order in which the operations of method 1100 are illustrated in FIG. 11 and described below is not intended to be limiting.

In some embodiments, method 1100 may be implemented using an exercise apparatus (see, e.g., exercise apparatus 102 of FIG. 1) including one or more processing devices (e.g., a digital processor, an analog processor, a digital circuit designed to process information, an analog circuit designed to process information, a state machine, a functionally limited processing device, and/or other mechanisms for electronically processing information), one or more user interface components configured to engage one or more body parts of a user and receive forces exerted by the user during performance of one or more exercises (see, e.g., user interface components 104 of FIG. 1), one or more sensors configured to generate output signals conveying information related to one or more parameters of muscular activity (see, e.g., sensors 106 of FIG. 1), one or more feedback components configured to provide feedback to a user (see, e.g., feedback components 108 of FIG. 1), and/or other components. The one or more processing devices may include one or more devices executing some or all of the operations of method 1100 in response to instructions stored electronically on an electronic storage medium. The one or more processing devices may include one or more devices configured through hardware, firmware, and/or software to be specifically designed for execution of one or more of the operations of method 1000.

Referring now to method 1100 in FIG. 11, at an operation 1102, forces exerted by a user during performance of one or more exercises may be received. In some implementations, operation 1002 may be facilitated by one or more user interface components the same as or similar to one or more user interface components 104 (shown in FIG. 1 and described herein).

At an operation 1104, output signals may be generated. The output signals may convey information related to one or more parameters of muscular activity of the user during the exercises. In some implementations, operation 1104 may be facilitated by a one or more sensors the same as or similar to one or more sensors 106 (shown in FIG. 1 and described herein). The one or more sensors may be coupled to individual ones of the user interface components.

At an operation 1106 values for the one or more parameters of muscular activity may be determined based on the output signals. The parameters may correspond to one or more of a muscle and/or muscle group activated by the user during performance of the given exercise, an amount of force exerted by the muscle and/or muscle group during the given exercise, an amount of repetitions of activation of the muscle and/or muscle group, an elapsed time of performance of the given exercise, an amount of calories burned, and/or other muscular activity. In some implementations, operation 1106 may be performed by one or more physical processors the same as or similar to the processors 110 (shown in FIG. 1 and described herein).

At an operation 1108, exercise instruction may be presented to a user. The instruction may correspond to coaching the user to continue exerting forces using a given muscle and/or muscle group or to exert forces using a different muscle and/or muscle group. In some implementations, operation 1108 may be facilitated by one or more feedback components the same as or similar to one or more feedback component 108 (shown in FIG. 1 and described herein).

Figure 12:
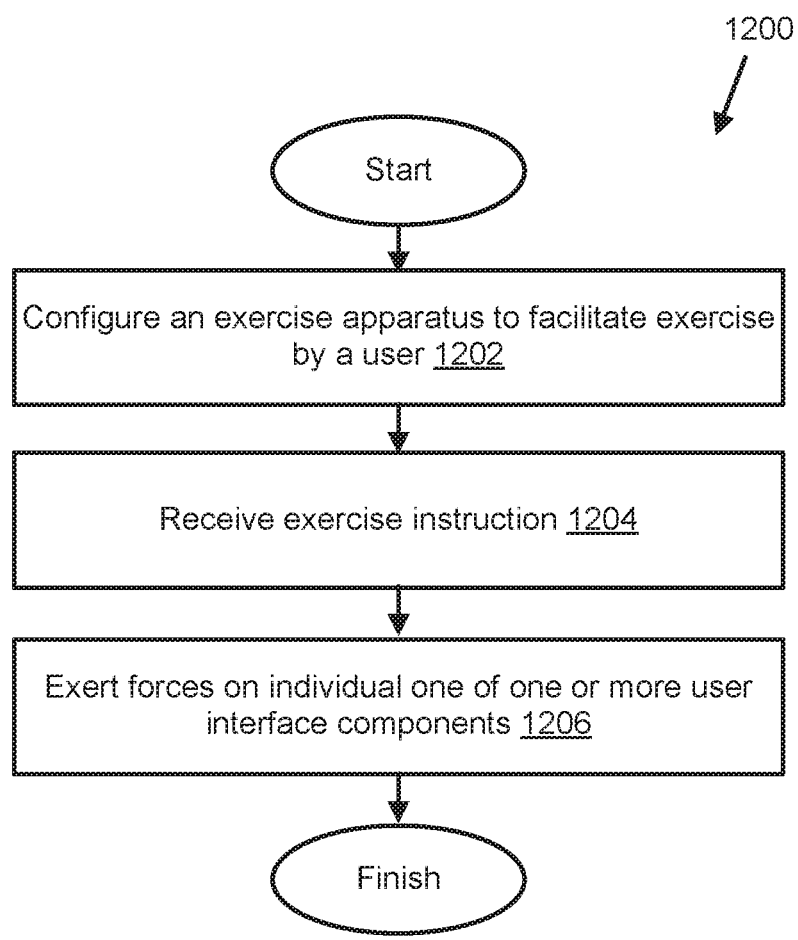
FIG. 12 illustrates a method of using an exercise apparatus, in accordance with one or more implementations.

FIG. 12 illustrates a method 1200 of using an exercise apparatus, in accordance with one or more implementations. The operations of method 1200 presented below are intended to be illustrative. In some embodiments, method 1200 may be accomplished with one or more additional operations not described, and/or without one or more of the operations discussed. Additionally, the order in which the operations of method 1200 are illustrated in FIG. 12 and described below is not intended to be limiting.

In some embodiments, method 1200 may be implemented by a user using an exercise apparatus (see, e.g., exercise apparatus 102 of FIG. 1) including one or more processing devices (e.g., a digital processor, an analog processor, a digital circuit designed to process information, an analog circuit designed to process information, a state machine, a functionally limited processing device, and/or other mechanisms for electronically processing information), one or more user interface components configured to engage one or more body parts of a user and receive forces exerted by the user during performance of one or more exercises (see, e.g., user interface components 104 of FIG. 1), one or more sensors configured to generate output signals conveying information related to one or more parameters of muscular activity (see, e.g., sensors 106 of FIG. 1), one or more feedback components configured to provide feedback to a user (see, e.g., feedback components 108 of FIG. 1), and/or other components.

Referring now to method 1200 in FIG. 12, at an operation 1202, an exercise apparatus may be configured to facilitate one or more exercises by a user. In some implementations, the exercise apparatus may be configured engaging a user in a substantially seated position. In some implementations, the exercise apparatus may be configured by moving and/or repositioning one or more user interface components that are configured to receive forces exerted by the user. In some implementations, the exercise apparatus may be configured by covering a structure with the exercise apparatus. A structure that may be covered by the exercise apparatus may include one or more of a floor, a chair, a stool, a car seat, a bench, a bed, a wall, and/or other structure. In some implementations, operation 1002 may be facilitated by an exercise apparatus the same as or similar to exercise apparatus 102 (shown in FIG. 1 and described herein), exercise apparatus 700 (shown in FIG. 7 and described herein), and/or exercise apparatus 800 (shown in FIG. 8 and described herein).

At an operation 1204, exercise instructions may be received. In some implementations, operation 1204 may be facilitated by one or more feedback components the same as or similar to one or more feedback component 108 (shown in FIG. 1 and described herein), one or more feedback components 712 (shown in FIG. 7 and described herein), and/or one or more feedback components 816 (shown in FIG. 8 and described herein).

At an operation 1206, forces may be exerted on one or more user interface components of the exercise apparatus. In some implementations, operation 1206 may be facilitated by one or more user interface components the same as or similar to one or more user interface components 104 (shown in FIG. 1 and described herein), one or more user interface components 708 (shown in FIG. 7 and described herein), and/or one or more user interface components 808 (shown in FIG. 8 and described herein).

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system for evaluating muscular activity exerted by a user during exercise and providing feedback to the user, the system comprising:
    an exercise apparatus comprising:
    one or more repositionable sensor configurations, wherein the user performs exercises using the apparatus by assuming one or more poses and applying forces on individual ones of the one or more repositionable sensor configurations;
    one or more sensors included with the one or more repositionable sensor configurations, the one or more sensors configured to generate output signals conveying information related to one or more parameters of muscular activity of the user during exercise, the one or more parameters of muscular activity include a muscle activation parameter corresponding to a muscle and/or muscle group activated by the user during exercise while assuming the one or more poses, a magnitude of force applied by the muscle and/or muscle group during exercise, an amount of repetitions of activation of the muscle and/or muscle group, an elapsed time of exercise performance, or an amount of calories burned; and
    one or more physical processors communicatively coupled to the one or more sensors and one or more feedback components, the one or more feedback components including a display screen configured to provide feedback to the user, and the one or more physical processors configured by computer-readable instructions to:
        obtain the generated output signals conveying information related to the one or more parameters of muscular activity;
        determine, based on the generated output signals obtained, values for the one or more parameters of muscular activity, the determined values comprising a quantification of applied force as a function of time;
        effectuate presentation of a calibration instruction via the one or more feedback components to the user during a calibration session, the calibration instruction configured to instruct the user to apply a maximum effort force and to assume a certain pose while applying the maximum effort force on the one or more repositionable sensor configurations;
        determine, based on the maximum effort force applied by the user during the calibration session, an exercise to be performed by the user; and
        effectuate presentation of the determined exercise via at least the display screen of the one or more feedback components, wherein the presentation of the determined exercise comprises:
            an exercise instruction portion providing exercise instruction relating to coaching the user to assume said certain pose and apply force over time on the one or more repositionable sensor configurations, and
            a gameplay portion representing magnitude of force that the user is expected to apply over time, the gameplay portion depicting vertically oriented obstacles, a path that represents a target force curve for the user to follow over time, the path being provided between the vertically orientated obstacles, and a game entity that represents a magnitude of current user applied force on the one or more repositionable sensor configurations,
            wherein said determined values are used as a control input to display and move the game entity along the path and over the vertically oriented obstacles on the display screen.

2. The system of claim 1, wherein at least some of the vertically oriented obstacles are arranged to oppose each other within the gameplay portion such that there is an opening therebetween for the user to guide the game entity therethrough via a change in said applied force over time.

3. The system of claim 2, wherein a width of said opening, a number of vertically oriented obstacles, and/or the magnitude of force to be applied over time is controllable by the user via a control element associated with the gameplay portion.

4. The system of claim 1, wherein the exercise apparatus comprises a thin flexible material.

5. The system of claim 1, wherein the one or more repositionable sensor configurations are movable relative to the exercise apparatus.

6. The system of claim 1, wherein the one or more repositionable sensor configurations are removably engageable to the exercise apparatus.

7. The system of claim 1, wherein the one or more sensors are configured to wirelessly couple to the one or more physical processors.

8. The system of claim 1, wherein the one or more feedback components further provide one or more of auditory feedback, tactile feedback, or olfactory feedback.

9. The system of claim 1, wherein the one or more feedback components are disposed at the exercise apparatus.

10. The system of claim 1, wherein the one or more physical processors comprise part of a mobile computing platform.

11. The system of claim 1, wherein the exercise apparatus is configured to cover one or more of a stool, a car seat, a bench, a bed, or a wall.

12. The system of claim 1, wherein the exercises performed by the user with the apparatus include isometric exercises performed by applying isometric forces on individual ones of the one or more repositionable sensor configurations.

13. A system for coaching a user performing one or more exercises, wherein the user performs exercises by exerting forces on individual ones of one or more user interface components coupled to an exercise apparatus, the system comprising:
   one or more physical processors configured by computer-readable instructions to:
   effectuate presentation of a calibration instruction via one or more feedback components including a display screen configured to provide feedback to the user during a calibration session, the calibration instruction configured to instruct the user to exert a maximum effort force and to assume a certain pose while exerting the maximum force on the one or more user interface components;
   obtain output signals generated from one or more sensors coupled to the one or more user interface components during the calibration session, the output signals conveying information related to the maximum effort force exertion;
   determine, based on the maximum effort force exerted by the user during the calibration session, an exercise to be performed by the user;
   effectuate presentation of the determined exercise via at least the display screen of the one or more feedback components, wherein the presentation of the determined exercise comprises:
      an exercise instruction portion providing exercise instruction relating to coaching the user to assume said certain pose and exert force on the one or more user interface components over time using one or more muscles and/or muscle groups, and
      a gameplay portion representing magnitude of force that the user is expected to exert over time, the gameplay portion depicting vertically oriented obstacles, a path that represents a target force curve for the user to follow over time, the bath being provided between the vertically oriented obstacles, and a game entity that represents a magnitude of current user exerted force on the one or more user interface components,
   obtain output signals generated from the one or more sensors during the determined exercise, the output signals conveying information related to one or more parameters of muscular activity of the user during the determined exercise on the display screen over time;
   determine values for the one or more parameters of muscular activity based on the output signals generated during performance of the determined exercise, the one or more parameters of muscular activity include a muscle activation parameter corresponding to a muscle and/or muscle group activated by the user, a magnitude of force exerted by the muscle and/or muscle group, an amount of repetitions of activation of the muscle and/or muscle group, an elapsed time of performance of the determined exercise, or an amount of calories burned, the determined values comprising a quantification of exerted force as a function of time, wherein the determined values are used as a control input to display and move the game entity along the path and over the vertically oriented obstacles on the display screen; and
   modify the presented exercise instruction on the display screen based on the determined values via presenting different instructional feedback, the modification corresponding to coaching the user to exert force using a different muscle and/or muscle group over time.

14. The system of claim 13, wherein at least some of the vertically oriented obstacles are arranged to oppose each other within the gameplay portion such that there is an opening therebetween for the user to guide the game entity therethrough via a change in said exerted force over time.

15. The system of claim 14, wherein a width of said opening, a number of vertically oriented obstacles, and/or the magnitude of force to be exerted over time is controllable by the user via a control element associated with the gameplay portion.

16. The system of claim 13, wherein the one or more physical processors are configured by computer-readable instructions to maintain an exercise history associated with the user based on the determined values, the exercise history reflecting changes in the determined values for the one or more parameters of muscular activity over time.

17. The system of claim 13, wherein the exercises performed by the user with the apparatus include isometric exercises performed by exerting isometric forces on individual ones of the one or more user interface components.

* * * * *